US007868072B2

(12) United States Patent  (10) Patent No.: US 7,868,072 B2
Sasahara et al.  (45) Date of Patent: Jan. 11, 2011

(54) GEL ADHESIVE COMPOSITIONS, METHOD OF MAKING, AND USE THEREOF

(75) Inventors: Shuichi Sasahara, Nara-ken (JP); Takahiko Fujita, Nara (JP); Kazuhiro Yoshikawa, Kashihara (JP)

(73) Assignee: Sekisui Plastics Co., Ltd., Osaka (JP)

( * ) Notice: Subject to any disclaimer, the term of this patent is extended or adjusted under 35 U.S.C. 154(b) by 89 days.

(21) Appl. No.: 11/547,051

(22) PCT Filed: Mar. 25, 2005

(86) PCT No.: PCT/JP2005/005551

§ 371 (c)(1), (2), (4) Date: Oct. 3, 2006

(87) PCT Pub. No.: WO2005/103186

PCT Pub. Date: Nov. 3, 2005

(65) Prior Publication Data

US 2007/0208130 A1  Sep. 6, 2007

(30) Foreign Application Priority Data

Apr. 22, 2004 (JP) ............................ 2004-127424

(51) Int. Cl.
*C08K 5/092* (2006.01)
(52) U.S. Cl. .................. 524/222; 524/221; 524/391
(58) Field of Classification Search .............. 524/500, 524/391, 221, 222
See application file for complete search history.

(56) References Cited

U.S. PATENT DOCUMENTS

| 4,588,762 | A | | 5/1986 | Mruk et al. |
| 4,674,512 | A | * | 6/1987 | Rolf ............................ 600/391 |
| 4,860,754 | A | | 8/1989 | Sharik et al. |
| 5,405,366 | A | * | 4/1995 | Fox et al. ....................... 607/50 |
| 6,592,898 | B2 | | 7/2003 | Munro et al. |
| 2001/0053897 | A1 | * | 12/2001 | Frate et al. ................... 604/304 |
| 2001/0055608 | A1 | * | 12/2001 | Hymes et al. ............... 424/443 |
| 2003/0171663 | A1 | * | 9/2003 | Munro et al. ............... 600/391 |

FOREIGN PATENT DOCUMENTS

| CN | 1267516 A | 9/2000 |
| JP | 57-115253 | 7/1982 |

(Continued)

OTHER PUBLICATIONS

Flick, Ernest W. (1990). Emulsifying Agents—An Industrial Guide. (pp. 142). William Andrew Publishing/Noyes.*

(Continued)

*Primary Examiner*—Milton I Cano
*Assistant Examiner*—John Uselding
(74) *Attorney, Agent, or Firm*—Cheng Law Group, PLLC

(57) ABSTRACT

A gel adhesive composition of the invention contains a crosslinked water-soluble polymer, water, a moisturizer, an amphipathic polymer, a water-insoluble polymer having adhesiveness, and an electrolytic salt and the composition contains the water-insoluble polymer in an amount of 3 to 20% by weight and the amphipathic polymer in an amount of 0.05 to 7.0% by weight with respect to the total amount of the composition except water.

18 Claims, 3 Drawing Sheets

FOREIGN PATENT DOCUMENTS

| | | |
|---|---|---|
| JP | 3-26777 | 2/1991 |
| JP | 2641146 | 5/1997 |
| JP | 9-509196 | 9/1997 |
| JP | 09-509196 | 9/1997 |
| JP | 9-313456 | 12/1997 |
| JP | 2001-181597 | 7/2001 |
| JP | 2002-80809 | 3/2002 |
| JP | 2002-212519 A | 7/2002 |
| JP | 2003-096431 | 4/2003 |
| JP | 2003-96431 | 4/2003 |
| JP | 2003-335805 | 11/2003 |
| JP | 2003-336024 | 11/2003 |
| JP | 2004-533520 | 11/2004 |
| JP | 2005-97408 | 4/2005 |
| JP | 2005-097408 | 4/2005 |

OTHER PUBLICATIONS

S. Murayama et al., "Hydrophobic and Hydrophilic Interpenetrating Polymer Networks (IPNS) Composed of Polystyrene and Poly (2-Hydroxyethyl Methacrylate) 2. Gradient Composition in the IPNS Synthesized by Photopolymer", Polymer vol. 34 (18), 1993 (paragraph 17 of p. 5) with the related parts marked in yellow.

International Search Report dated May 17, 2005 with English translation.

Notification of First Office Action for the Application No. 200580012484.0 from Patent Office of the People's Republic of China dated Apr. 10, 2009.

* cited by examiner (a)

(b)

(c)

(a)

(b)

(c)

GEL ADHESIVE COMPOSITIONS, METHOD OF MAKING, AND USE THEREOF

This application is a 371 of international application PCT/JP2005/05551 filed Mar. 25, 2005, which in turn claims priority to JP 2004-127424 filed Apr. 22, 2004.

CROSS REFERENCE TO RELATED APPLICATIONS

This application claims priority to Japanese Patent Application No. P2004-127424, filed on Apr. 22, 2004, the entire disclosure of which is incorporated herein by reference in its entirety.

FIELD OF THE INVENTION

The present invention relates to gel adhesive compositions, a method for manufacturing the same, and an electrode using said gel adhesive compositions. In particular, the present invention relates to gel adhesive compositions preferably be used for adhesives for bio-patch.

BACKGROUND OF THE INVENTION

The following description sets forth the inventor's knowledge of the related art and problems therein and should not be construed as an admission of knowledge in the prior art.

Conventional adhesives including natural rubber latex and acrylic ester resins are so-called oleaginous adhesives. Because they have strong water repellent properties, oleaginous adhesives neither absorb nor transmit water when applied to an organism for a extended time, particularly during perspiration. Instead, the water is stored between the skin surface and the adhesive tape, causing sweating and rashes. In addition, during profuse perspiration, adhesion sometimes decreases. Further, the adhesives may not adhere to wet surfaces of adherence object. Therefore, it is difficult to apply the tape until the wet surface is wiped or dried.

Also, it is difficult to use oleaginous adhesives as conductive adhesives on an electrode for use on an organism, for example electrocardiogram electrodes or electrodes for performing electric stimulation of low or middle frequency treatment. Instead, hydrogel adhesives commonly are used.

However, conventional hydrogels have several problems. For example, although hydrogels exhibit strong adhesion to strongly hydrophilic materials such as paper, cotton, and the like, hydrogels exhibit detachability rather than adhesion to oleaginous materials such as olefin films and the like. Because sebum, which is oleaginous rather than hydrophilic, usually exists on the surface of human skin, adhesion of hydrogels with highly hydrophilic properties to the skin is limited. In particular, because initial tackiness after application is weak, the applied position of the adhesive may become misaligned or the adhesive may detach immediately after the adhesive tape is applied to the organism. Therefore, additional attachment means are necessary such as temporary fixation with other adhesives. Consequently, hydrogels have been difficult to apply in the medical field.

Furthermore, when electrodes are placed on an organism, they are often placed in pairs with set intervals or distances separating the electrodes. For example, electrodes for measuring body fat percentage that can be applied at certain intervals are known. Specifically, the electrode may have a structure in which a pair of electrode element portions are formed of a conductive material on the surface of a non-conductive substrate sheet. An electrode terminal portion may be formed integrally with the pair of electrode element portions and a conductive adhesive gel layer may be applied on said pair of electrode element portions (see, e.g., Japanese Unexamined Laid-open Patent Publication No. Hei 9-313456).

The electrode for measuring body fat percentage is used by closely contacting the electrode with the skin of a person. The person's body fat percentage is measured by applying a weak current to the body and measuring the electric resistance. For this reason, the electrode for measuring body fat percentage is provided with a structure in which pairs of electrode element portions with intervals of about 10 to about 100 mm are coated with conductive adhesive layers to effect close contact between the electrode element portions and the skin. In order to keep the distance between electrode element portions constant, non-stretchy and comparatively flexible films such as polyethylene terephthalate (PET) preferably are used as the substrate sheet.

Improved adhesiveness of the hydrogels is required in other uses as well. For example, in order to increase initial tackiness, softening a gel has been described. However, when the gel is softened enough to obtain satisfactory initial tackiness, workability of the gel, such as cutting and the like, decreases. This may result in many problems, for example the gel may protrude from the processed product and adhere to wrapping bags and the like; during use, the gel may adhere to clothes or break; furthermore, the gel may protrude from the slit surface during storage; moreover, dust adheres to the gel.

A method of enhancing adhesive properties of the hydrogels other than softening the gel includes the use of non crosslinkable polyvinyl pyrrolidone as a tackifier (see, e.g., Japanese Unexamined Laid-open Patent Publication No. Hei 3-26777 and U.S. Pat. No. 4,860,754). In more detail, the invention relates to a conductive adhesive material comprising low-molecular-weight plasticizers selected from non-volatile alcohols and polyhydric alcohols; high-molecular-weight water soluble crosslinkable polymers which are soluble in said low-molecular-weight plasticizers; tackifiers comprising non crosslinkable polyvinyl pyrrolidone; and a satisfactory amount of an electrolyte dopant for imparting conductivity to said adhesive material.

However, polyvinyl pyrrolidone is water-soluble and hydrophilic. Because polyvinyl pyrrolidone does not have a satisfactory affinity for sebum and the like, it is difficult to demonstrate strong adhesion after application to skin.

In order to impart initial tackiness, methods are disclosed such as adding hydrophobic polymers to hydrogels, compounding polyhydric alcohols and water in a matrix of hydrophilic polymer. These hydrophobic polymers are adhesives and have good affinity to sebum and the like and are capable of realizing strong adhesion. For example, an adhesive hydrogel comprising glycerin, water, vinyl acetate-dioctyl maleate copolymer, and methyl salicylate in a matrix with synthetic resins such as polyacrylic acid, polyacrylamide, and the like as a skeleton structure is disclosed by Japanese Unexamined Laid-open Patent Publication No. Sho 57-115253. Among these compositions, vinyl acetate-dioctyl maleate copolymer are hydrophobic polymers and adhesives. These hydrophobic polymers are stated to strengthen the adhesion. Vinyl acetate-dioctyl maleate copolymer is sold, for example, under the trade name "Flexbond 150" by Air Products and Chemicals, Inc.

U.S. Pat. No. 4,588,762 discloses conductive adhesives for biomedical electrodes in which a hydrophilic layer comprising water, an electrolyte, and humectants and a viscoelastic polymer layer that substantially is a hydrophobic polymer is placed in dispersal stability. Said humectants comprise 30% to 60% by weight of water, 5% to 35% by weight of latex emulsion (with a polymer solid content of 50%), 10% to 30% by weight of humectants (glycerin and the like), 1% to 10% by weight of electrolyte, and 0.2% to 10% by weight of aqueous polymer, with a tackifier and a film processability improving agent added to enhance adhesion. An exemplary latex emulsion is "Flexbond 150" sold by Air Products and Chemicals, Inc, as mentioned in Japanese Unexamined Laid-open Patent Publication No. Sho 57-115253.

In the above mentioned hydrogels a hydrophobic polymer emulsion dispersed by emulsification is added to a hydrophilic matrix. In order to form a hydrophilic matrix, a previously polymerized synthetic or natural polymer and other compounding components are mixed and crosslinked using, for example, metal or radiation.

Compositions of polymer materials that form interpenetrating polymer networks (IPNs) of polysiloxane (1) and acryl (2) also are known (see, e.g., Japanese Examined Laid-open Patent Publication No. 2641146). In generating the IPNs, a mixture of the monomers and a polymerization initiator or the like is required. The polysiloxane and acryl monomers are poured into a die, thereby reacting them. A network of polysiloxane (1) forms first and then a network of acryl (2) is generated by heating the mixture. It further is stated that the wetting property against water is remarkably low, with respect to the surface characteristics of a product obtained by annealing the aforementioned polymer materials.

The stated reason is that the surface of above mentioned products is composed of a layer of network (1) with a thickness of 5 nm and that even when this surface layer comes off due to wear, the layer recovers to the initial surface state by heating in a short time.

Murayama et al. report that other mixtures of polymers or graft polymer, also in IPN, generate a concentration gradient between a surface and an inner portion (see, e.g., Murayama, S. et al, "Hydrophobic and hydrophilic interpenetrating polymer networks (IPNs) composed of polystyrene and poly(2-hydroxyethyl methacrylate) 2. Gradient composition in the IPNs synthesized by photopolymerization", Polymer Vol 34 (18), 1993). Therefore, the characteristics stated in patent document 6 (Japanese Examined Laid-open Patent Publication No. 2641146) prove the physiochemical phenomena as well.

Further, regarding the mixture of said hydrophilic polymer and hydrophobic polymer, it is thought that affinity to sebum is further strengthened by bleeding of the hydrophobic polymer layer whose surface free energy is lower. However, not in the case of IPN as stated in the above mentioned Patent Document 6 (Japanese Examined Laid-open Patent Publication No. 2641146) and the like, in the case of a mixture of hydrophilic polymer and hydrophobic polymer, or further when it is the case that the hydrophilic polymer is crosslinked and the hydrophobic polymer is in the state of dispersion by emulsification, the concentration gradient between a surface and an inner portion is generated for a shorter period of time.

Including a hydrophobic adhesives and latex in the hydrophilic polymer matrix or emulsifying and dispersing a hydrophobic adhesives and latex in the hydrogel may help to rectify the hydrogel's low affinity to sebum and weak initial tackiness without damaging other beneficial characteristics of the hydrogel such as mild property and conductivity.

U.S. Pat. No. 6,592,898 discloses a hydrogel comprising a hydrophobic polymer in a hydrophilic polymer matrix wherein the concentration of the hydrophobic polymer at the surface of the gel is greater than the concentration of the hydrophobic polymer inside the gel. Adhesion of the bioadhesive composition is greater at the surface than inside of the gel due to the higher concentration of hydrophobic polymer at the surface of the gel.

As mentioned above, in a gel adhesive composition, improvement in adhesiveness is required both for the use as electrodes and for the use as materials other than electrodes.

For example, in the electrode for measuring body fat percentage, a conductive adhesive gel layer is formed on an electrode element portion. The area of adhesion to the human body is smaller than the whole area of the electrode for measuring body fat percentage. In order to improve adhesion to the skin, it is desired to form an adhesive gel layer on portions of the electrode for measuring body fat percentage other than the electrode element portion, for example, on polyethylene terephthalate.

However, because a conductive gel adhesive layer primarily comprises water and hydrogel that stably retains moisturizer and an electrolyte as required in a hydrophilic resin matrix, it has a weak adhesiveness to the polyethylene terephthalate substrate sheet although it has good adhesiveness to an electrode element portion which is obtained by a paste mainly composed of polyester or polyurethane series resin including carbon. When peeled off from the skin, delamination between the substrate sheet layer and the conductive gel adhesive layers occurs.

In other words, it is difficult to obtain gel adhesive compositions that have strong adhesion both to polyethylene terephthalate and skin.

Even in the case where the electrode is not limited to an electrode for measuring a body fat, by including hydrophobic polymer components in a hydrophilic polymer matrix, improved adhesion is attained. Though inclusion of hydrophobic adhesives and latex in a hydrophilic polymer matrix to obtain hydrogel adhesives with a high affinity to sebum and strong initial tackiness to the skin is known, it is difficult to uniformly disperse and stabilize hydrophobic adhesives in a hydrogel having strongly hydrophilic properties.

As mentioned, there are two primary methods for forming a hydrogel structure that includes hydrophobic adhesives. The first method (A) involves mixing adhesives with a highly viscous solution or paste of a natural or synthetic polymer that was previously polymerized. The dispersed mixture is coated and molded into a sheet form and crosslinked by exposure to radiation and the like to generate a gel. The other method (B) involves emulsifying and dispersing hydrophobic adhesives in a monomer-mixed solution before polymerization. The monomer/hydrophobic adhesive mixture is exposed to light in order to initiate polymerization and cross linking to generate a gel.

In either method, the pre-mixed solution primarily is composed of hydrophilic components and water. Therefore, it is preferable that the hydrophobic adhesives to be added to the pre-mixed solution are added in the form of an emulsion which is emulsified and dispersed in water beforehand. Although method A has the advantage in that the pre-mixed solution has high viscosity and the added emulsion is hard to separate with time, it is difficult to uniformly disperse the emulsion in the pre-mixed solution and the generation of some granular aggregates cannot be avoided. If a stirring method applying a high sheer force is used to destroy the granular aggregates, not only will the emulsion particles be destroyed, but also molecular chains of the polymer which is to be the matrix structure are destroyed. High sheer force stirring thereby risks deteriorating various post-crosslinked gel properties. Therefore, where the post-crosslinked gel properties are to be preserved, some granular aggregates are permitted to exist in the gel, thereby forming a nonuniform gel structure. In method B, while there is advantageous very little risk that granular aggregates will be generated, when the stirring stops, the added emulsion easily separates and the uniformity of the pre-mixed solution is damaged in a short time. In addition, method A does not ensure that the mixture will not separate, though separation occurs more slowly with method A than with method B.

Gels formed in a state where the pre-mixed solution is separated have variable emulsion contents. Since the other composition is also uneven depending on a portion, a gel has very unstable qualities. Further, with the passage of time, the separation state of the pre-mixed solution changes, which increases the variation in the emulsion content of the gel.

Separated pre-mixed solution may sometimes be re-dispersed by re-stirring. In many cases, however, particles of the emulsion become bonded to one another, resulting in increased particle diameters or coagulation, which are irreversible processes. Therefore, countermeasures to prevent the separation of the pre-mixed solution should be taken, for example conducting gelation right after the preparation of the pre-mixed solution or by continuously stirring after the preparation to gelation.

However, in taking these countermeasures, minimum dispersal stability is needed. Even when continuously stirring, this cannot be the preferable method physically and economically, however, because many factors need to be considered, such as containment size, shapes, stirring method, speed and the like. Further, when a gel structure is formed while stirring, large amounts of air bubbles may be mixed into the gel, or, depending on the kinds of monomers used, the amount of dissolved oxygen may change, thereby causing the reactivity and physical properties of the gel to change.

Regarding the B method, although methods such as adding hydrophilic polymer to lower the separation speed or regulating viscosity by adding aqueous plasticizer used as moisturizer may be utilized, it is necessary to be careful when adding a viscosity regulator that emulsion dispersion is inhibited and coagulation is generated. Further, adding salt to the gel to provide conductivity risks salting out and complete separation and coagulation of the gel. This reveals that the process of generating particle mass by taking the A method progresses at an accelerating speed in pre-mixed solution with high fluidity.

In addition, said moisturizer, besides regulating viscosity of the pre-mixed solution, has the important role of maintaining the moisture content of the gel. Therefore, unless a certain amount of moisturizer is compounded, the gel finally obtained has a low moisture content, dries out quickly, has weak adhesion properties, and deteriorating electrical impedance properties.

In other words, because in gel adhesive compositions disclosed in above-mentioned documents that include hydrophobic resin in a hydrophilic polymer matrix hydrophobic resin is easily separated in pre-mixed solution in the production process without continuous stirring, gel adhesive compositions that are strongly adhesive to oleaginous surfaces cannot easily be obtained and continuous manufacturing of the gel adhesive compositions is difficult.

The description herein of advantages and disadvantages of various features, embodiments, methods, and apparatus disclosed in other publications is in no way intended to limit the present invention. Indeed, certain features of the invention may be capable of overcoming certain disadvantages, while still retaining some or all of the features, embodiments, methods, and apparatus disclosed therein.

The preferred embodiments of the present invention have been developed in view of the above-mentioned and other problems in the related art. The preferred embodiments of the present invention can significantly improve upon existing methods and/or apparatuses.

Among other potential advantages, the object of the present invention is to provide gel adhesive compositions which are excellent in adhesion. In particular, the object of the present invention is to provide gel adhesive compositions having good adhesion to both substrate sheet surfaces which are polyethylene terephthalate surfaces and carbon coat surfaces which are electrode element portions.

In addition, the object of the present invention is to provide gel adhesive compositions and method of manufacturing the same having excellent adhesion to a skin surface of a human body. Further, the object of the present invention is to provide electrodes which include these gel adhesive compositions as conductive gel adhesive layers.

SUMMARY OF THE INVENTION

To solve the above-mentioned problems, the present invention provides a gel adhesive composition containing a crosslinked water-soluble polymer, water, a moisturizer, and an amphipathic polymer and in which the amphipathic polymer is contained in an amount of 0.05 to 7.0% by weight with respect to the total amount of the composition except water.

As one embodiment of the present invention, it is preferable that the gel adhesive composition further contains a water-insoluble polymer having adhesiveness in an amount of 3% by weight or more with respect to the total amount of the composition except water.

As another embodiment of the present invention, it is preferable for the gel adhesive composition that the crosslinked water-soluble polymer composes a matrix of the composition.

The gel adhesive composition of the present invention is obtained preferably by a manufacturing method comprising the following steps: (a) mixing a pre-mixed solution containing a non crosslinkable monomer, a crosslinkable monomer, a moisturizer, water, a water-insoluble polymer, and an amphipathic polymer and (b) carrying out polymerization by heating or radiating light to the mixed pre-mixed solution.

Since the gel adhesive composition of the present invention contains the amphipathic polymer therein and therefore has good sticking property even to a carbon-coated face and polyethylene terephthalate face, the gel adhesive composition is not separated from an electrode surface and even in the case of repeated use, it is excellent in adherence property to a skin face of a human body. Further, in the case the gel adhesive composition of the invention contains the water-insoluble polymer therein, there is provided the gel adhesive composition having no granule agglomerates of the water-insoluble polymer and containing the respective components in evenly dispersed state and excellent in adhesiveness.

Additionally, in the case the composition contains the moisturizer in an amount of 50% by weight of more with respect to the total amount of the composition except water, the obtained gel is hardly dried and excellent in stability.

Further, according to the manufacturing method of the present invention, it is made possible to obtain a gel adhesive composition having adhesiveness and stability in the form of an emulsion without requiring the above-mentioned countermeasure to separation and agglomeration for a prescribed period from the time of production of the pre-mixed solution in which the water-insoluble polymer is emulsified and dispersed, so that the physical property dispersion among portions or lots of products can be extremely narrow and the obtained gel adhesive composition is provided with stable qualities. Further, the pre-mixed solution is excellent in storage stability, as described above, it can be stored and transported as it is and thus the pre-mixed solution is very easy to handle.

In the case the gel adhesive composition of the present invention stably contains the water-insoluble polymer, which has a role as a hydrophobic adhesive, the composition has a high affinity with the sebum and particularly high initial tackiness to the skin and moreover since the composition contains the crosslinked water-soluble polymer, it has a hydrogel matrix. Accordingly, the gel adhesive composition gives a highly capable adhesive with a suppressed stimulus property to the skin.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The preferred embodiments of the present invention are shown by way of example, and not limitation, in the accompanying figures, in which:

FIG. 1(a) is a plane view of the embodiment: FIG. 1(b) is a cross-sectional view along the line A-A in FIG. 1(a): and FIG. 1(c) is a patterned drawing showing the relation between the PET region and the carbon-coat-region in FIG. 1(a);

FIG. 3(a) is a side view of the embodiment: FIG. 3(b) is a front view of the gel adhesive layer side: FIG. 3(c) is a front view of the electrode of another embodiment in the gel adhesive layer side different from that of FIG. 3(b).

DETAILED DESCRIPTION OF THE EMBODIMENTS

Figure 1:
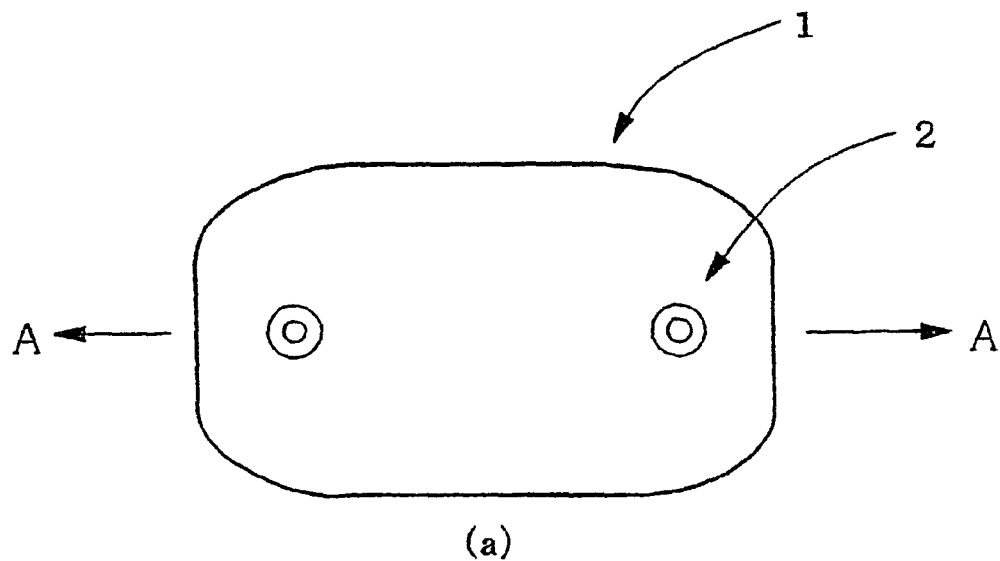
FIG. 1 is a drawing showing an electrode of the first embodiment using a gel adhesive composition according to the present invention.
Figure 1:
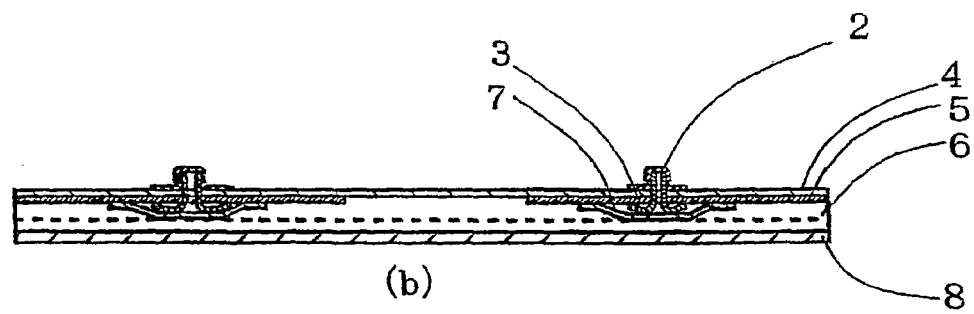
Figure 1:
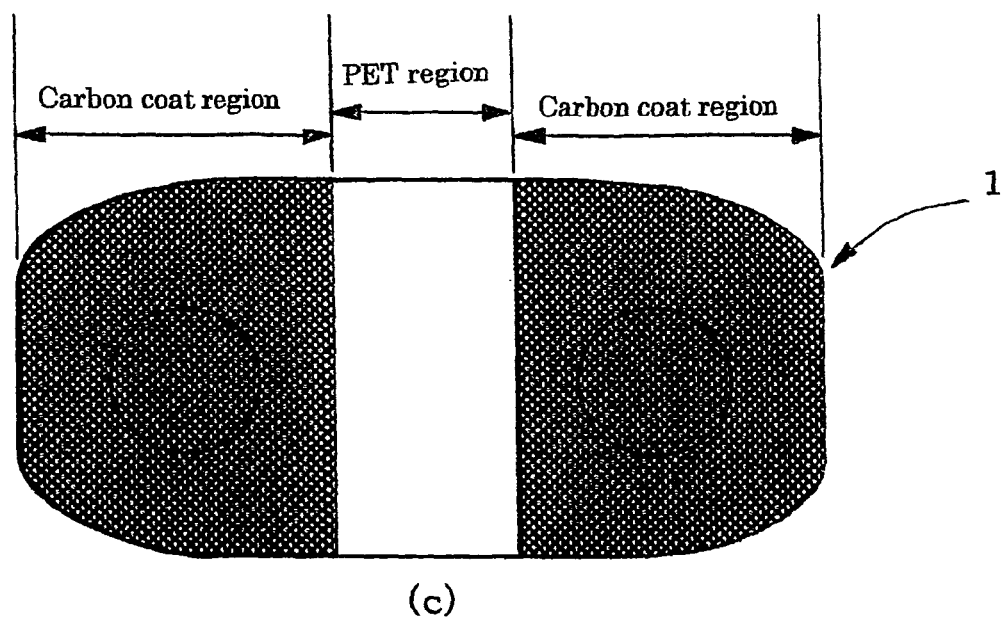

In the following paragraphs, some preferred embodiments will be described by way of example and not limitation. It should be understood based on this disclosure that various other modifications can be made by those of average skill in the art based on these illustrated embodiments.

The present invention is a gel adhesive composition containing a crosslinked water-soluble polymer, water, a moisturizer, and an amphipathic polymer and in which the amphipathic polymer is contained in an amount of 0.05 to 7.0% by weight with respect to the total amount of the composition except water.

A preferable manufacturing method of the invention is a method for manufacturing the gel adhesive composition comprising the following steps: (a) mixing a pre-mixed solution containing a non crosslinkable monomer, a crosslinkable monomer, a moisturizer, water, a water-insoluble polymer, and an amphipathic polymer and (b) carrying out polymerization by heating or radiating light to the mixed pre-mixed solution.

Crosslinked Water-Soluble Polymer

A crosslinked water-soluble polymer to be used in the present invention is not particularly limited if it is a water-soluble polymers containing crosslinked parts. The water-soluble polymer can be obtained in the form of a copolymer of a non crosslinkable monomer and a crosslinkable monomer. For example, a copolymer of a water-soluble (meth)acrylic monomer and a crosslinkable monomer having two or more alkenyl groups can be used. As the (meth)acrylic monomer, (meth)acrylic monomers such as (meth)acrylamide, N-alkyl-modified (meth)acrylamide, N,N-dialkyl-modified (meth)acrylamide, (meth)acrylic acid, and alkyl(meth)acrylate and the like can be exemplified. As the crosslinkable monomer having two or more alkenyl groups, crosslinkable monomers such as polyfunctional acrylates, polyfunctional acrylamides can be exemplified. The gel adhesive composition of the invention can compose a matrix of the water-soluble polymer by the crosslinked water-soluble polymer. That is, the gel adhesive composition of the invention is a gel adhesive composition containing a crosslinked water-soluble polymer, water, a moisturizer, and an amphipathic polymer and of which water, the moisturizer, and the amphipathic polymer are contained in the matrix in the water-soluble polymer.

Specific examples of non crosslinkable monomers that compose water-soluble polymers include, for example, non-electrolyte acryl amide derivatives such as (meth)acryl amide, N-methyl(meth)acryl amide, N-ethyl(meth)acryl amide, N-propyl(meth)acryl amide, N,N-dimethyl(meth)acryl amide, N,N-diethyl (meth)acryl amide, acryloyl morpholine, and the like; electrolyte series acryl amide derivatives such as tertial butyl acryl amide sulfonic acid (TBAS) and (or) salts thereof, N,N-dimethyl aminoethyl acrylamide (DMAEAA) hydrochloride salt, and the like; electrolyte series acryl derivatives such as (meth)acrylate, maleic acid, itaconic acid, sulfopropyl methacrylate (SPM) and (or) salts thereof, methacryloyl oxyethyl trimethyl ammonium chloride (QDM), and the like; and non-electrolyte series acryl derivatives such as hydroxylethyl(meth)acrylate, polyethylene glycol (meth)acrylate, and the like.

Specific examples of crosslinkable monomers include N,N'-methylene bis (meth) acryl amide, ethylene glycol di(meth)acrylate, polyethylene glycol di(meth)acrylate, glycerin tri(meth)acrylate, and the like.

The content of the crosslinked water-soluble polymer in the gel adhesive composition of the present invention is not particularly limited if the non crosslinkable monomer and the crosslinkable monomer are evenly dissolved in the case of producing the pre-mixed solution containing the non crosslinkable monomer and the crosslinkable monomer. The crosslinked water-soluble polymer is contained preferably in an amount of 15% by weight or higher and more preferably 18% by weight or higher with respect to the total amount of the gel adhesive composition except water in order to maintain the gel strength and heighten the shape holding property and processability of a gel to be obtained. To form the matrix of the gel adhesive composition using the crosslinked water-soluble polymer, the non crosslinkable monomer is used and the non crosslinkable monomer is mainly water soluble and has a sufficiently high solubility in water and particularly, in the case of a monomer in liquid phase at a normal temperature, a monomer to be dissolved in water at an optional ratio is preferable. On the contrary, it is sometimes needed to dissolve a moisturizer and, based on necessity, an additive such as an electrolytic salt and a polymerization initiator other than water and the monomer in the gel adhesive composition and such a case, the concentration of the crosslinked water-soluble polymer in the gel adhesive composition is set to be preferably 35% by weight or lower and more preferably 30% by weight or lower with respect to the total amount of the gel adhesive composition except water.

Although the content of said crosslinkable monomer with respect to the total amount of the gel adhesive compositions should approximately be set depending on the molecular weight or chemical or physical property of above mentioned non crosslinkable monomer and said crosslinkable monomer, in order to enhance the shape keeping ability of the obtained gel, it is preferable that the ratio is not less than 0.01% by weight, and more preferably, not less than 0.05% by weight. Meanwhile, because initial tackiness used for adhesives can easily be obtained with flexibility to a degree that shape keeping ability is not damaged, it is preferable that the ratio is not greater than 1.0% by weight, and more preferably, not greater than 0.6% by weight.

As mentioned above, because the above mentioned non crosslinkable monomer is the primary part of the matrix, it is preferable that the monomer has high water-solubility. For example, the solubility of the monomer in water preferably is not less than 20 (g/100 g $H_2O$), and more preferably, not less than 50 (g/100 g $H_2O$), and most preferably, not less than 65 (g/100 g $H_2O$).

Because the above mentioned crosslinkable monomer forms a part of the matrix, the hydrophilic property of the matrix as a whole is not damaged even if the crosslinkable monomer is not water-soluble. Methods for dissolving a crosslinkable monomer with low water-solubility in the above mentioned pre-mixed solution include, for example, dissolving in non crosslinkable monomer and other than dissolving in non crosslinkable monomer, methods also include dissolving in polyvalent alcohol when crosslinkable monomer is liquid.

It is preferable that the gel adhesive compositions of the present invention include a moisturizer in order to enhance moisturizing properties and plasticity. As a moisturizer, it is preferable to include polyhydric alcohols in the gel adhesive compositions. Suitable polyhydric alcohols for use in embodiments include other than diols such as ethylene glycol, propylene glycol, butane diol, polyhydric alcohols such as glycerin, pentaerythritol, sorbitol and the like; polyhydric alcohol condensed components such as polyethylene glycol, polypropylene glycol, polygricerine and the like; polyhydric alcohol modified product such as polyoxy ethylene glycerin and the like. In addition, as a moisturizer, it is preferable to use liquid polyhydric alcohols at a room temperature (preferably, not less than minus 10° C.), more preferably, liquid polyhydric alcohols within the temperature range at which the gel is actually used (for example, when the gel is used in the room, around 20° C.).

Since the gel adhesive compositions of the present invention include water, without a moisturizer, it is liable to vaporize or dry out in a short time, thereby damaging plasticity and, at the same time, adhesiveness. In particular, initial tackiness is liable to lower remarkably. In addition, when the gel adhesive compositions of the present invention are implemented for a use requiring conductivity such as for biomedical electrodes, when water vaporizes, impedance of electrodes increases and, further, when impedance of electrodes exceeds the specific value, it cannot be used. Therefore, a moisturizer works to prevent vaporization exceeding a certain amount of water when the moisturizer is added to gel adhesives, and if said moisturizer is in a liquid state at a room temperature, the moisturizer itself may also function as a plasticizer.

It is preferable that the concentration of a moisturizer in the gel adhesive compositions is not less than 50% by weight with respect to the amount excluding water from the total amount of the said gel adhesive compositions in order to maintain moisturizing property and plasticity and to show excellent stability. It further is preferable that the concentration of a moisturizer in the gel is not less than 55% by weight. Further, it is preferable that the concentration of this moisturizer is not greater than 80% by weight with respect to the amount excluding water from the total amount of the said gel adhesive compositions, more preferably not greater than 75% by weight, to secure a certain amount of resin solid content to ensure the flexible strength and adhesion of the gel.

Water

It is preferable that the concentration of water to be contained in the gel adhesive compositions is not less than 13% by weight in the above mentioned monomer-mixed solution in order to stably dissolve the water-insoluble polymer having adhesiveness, in other words, not less than 13% by weight with respect to the total amount of said gel adhesive compositions and more preferably, not less than 18% by weight. In addition, in order to inhibit the change of the gel's properties by vaporization and drying, and stabilize the gel's properties, it is preferable that the amount of water is not greater than 40% by weight in the monomer-mixed solution, or in other words, with respect to the total amount of said gel adhesive compositions, and more preferably, not greater than 30% by weight. For example, in the case of glycerin, it has the moisturizing property of retaining water of about 20 to 40% by empty weight and with relative humidity of about 50% to 70%. Furthermore, the inventors prepared hydrogels comprising each kind of moisturizers and found out the moisturizing property with the relative humidity of 60%, for example, the moisturizing property of glycerin was about 30% by weight, while the moisturizing property of sodium lactate was about 80% by weight.

As seen above, the moisturizing property of a moisturizer depends on relative humidity and the moisturizing property of the hydrogels using a moisturizer also depends on relative humidity. By using moisturizers having different moisturizing abilities in combination, the moisturizing property of the gel at a certain humidity can be controlled, however, because dependability of relative humidity is a characteristic peculiar to a moisturizer, it is substantially impossible to control. As heretofore mentioned, preferably, using a moisturizer having low moisturizing property (more preferably, it is in a liquid state at a room temperature) in high concentration and setting moisture content low enables to lower the relative humidity dependence of a moisturizing property of a gel by appearance, however, it is preferable for gel adhesive compositions to retain moisture content having the same concentration as above or higher in order to stably disperse water-insoluble polymer having adhesiveness.

Water-Insoluble Polymer

As the water-insoluble polymers having adhesiveness, polymerization of one or more hydrophobic monomers such as hydrophobic monomer alone or polymerizations thereof such as (meth)acryl ester, vinyl acetate, maleic acid ester and the like are exemplified. To be specific, hydrophobic monomer alone or copolymer thereof such as isooctyl(meth)acrylate, 2-ethyl hexyl (meth)acrylate, butyl(meth)acrylate, vinyl acetate, dioctyl maleate and the like, and others may include one of hydrophobic monomers such as ethylene, propylene, butylene, methyl(meth)acrylate, ethyl(meth)acrylate, and the like or copolymerization thereof. Further, silicone adhesives or natural or synthetic rubber adhesives can be used. Among these, acrylic ester copolymer is preferably used since it has been improved and proven to be highly adhesive as well as less irritable to the skin.

In order to disperse the water-insoluble polymer having adhesiveness in hydrogels, it is preferable to use an emulsion in which said polymer is emulsified and dispersed. Usually, the solid content of said emulsion is 30% to 60% by weight and the most of the remaining portion is water.

For example, as emulsions of acrylic ester copolymer resins, "POLYZOL PSA SE-1730" manufactured by Showa Polymer Co., Ltd., "VINYBLAN ADH-1048" manufactured by Nissin Chemical Industry Co., Ltd. and the like preferably can be used.

Although the contained amount of the water-insoluble polymer having adhesiveness in the gel adhesive compositions may be adjusted depending on effects expected for the final products, in order to obtain such effects as can be judged by the difference of human tactile sensation, it is preferable to add not less than 3% by weight expressed in terms of solid with respect to the amount excluding water from the total amount of said gel adhesive compositions. Further, since these polymers alone have functions as adhesives, much added amount is available, however, considering the balance with other hydrophilic components to prepare gel adhesive compositions, it is preferable to be not greater than 20% by weight with respect to the amount excluding water from the total amount of said gel adhesive compositions, and more preferably 15% by weight.

Further, it is preferable that the water-insoluble polymer having adhesiveness is a copolymer of said hydrophobic monomer and hydrophilic monomer. By copolymerizing the hydrophilic monomer with hydrophobic monomer, it has the advantage in that dispersal stability of the water-insoluble polymer is improved and the added amount of a dispersant, a surfactant, and the like can be kept less.

When the adhesive water-insoluble polymer is a copolymer of hydrophobic monomer and hydrophilic monomer, the effect of dispersal stability is demonstrated when the copolymerization ratio of hydrophilic monomer in said copolymer is not less than 0.1% by weight. In addition, Japan Unexamined Patent Publications 2002-80809, 2003-336024, and 2003-335805 state that when the copolymerization ratio exceeds 5% by weight, the polymer is difficult to generate. Therefore, as said water-insoluble polymer, it is preferable to use copolymer of hydrophobic monomer and hydrophilic monomer having copolymerization ratio of said hydrophilic monomer of 0.1 to 5% by weight.

As said hydrophilic monomers, water-soluble monomers of hydroxyethyl (meth)acrylate, polyethylene glycol (meth)acrylate, (meth)acryl amide, N-methyl (meth)acryl amide, N-ethyl(meth)acryl amide, N-propyl(meth)acryl amide, N,N-dimethyl (meth)acryl amide, N,N-diethyl(meth)acryl amide, acryloyl morpholine, tert-butyl acryl amide sulfonic acid (TBAS) and (or) salt thereof, N,N-dimethyl amino ethyl acryl amide (DMAEAA) hydrochloride salt, N,N-dimethyl amino propyl acryl amide (DMAPAA) hydrochloride salt, (meth)acrylic acid, maleic acid, itaconic acid, sulfo propyl methacrylate (SPM) and (or) salt thereof, methacryloiloxyethyl trimethyl ammonium chloride (QDM) and the like are exemplary. Among these, it is desirable to contain water-soluble monomer comprising at least one species of carboxylic group and in particular, (meth)acrylic acid and (or) the salt thereof generally are used as the monomer and they can preferably be used, and among them, acrylic acid alkyl ester is preferable.

pH Regulator

The gel adhesive compositions of the present invention can be obtained by copolymerization reaction by heating or exposing the monomer-mixed solution to light that comprises at least a monomer, a crosslinkable monomer, a moisturizer, water, an amphipathic polymer, and a polymerization initiator. In other words, as aforementioned, the present invention relates to a manufacturing method of gel adhesive compositions including the following process. (a) a process of mixing pre-mixed solution which includes non crosslinkable monomer, crosslinkable monomer, moisturizer, water, water-insoluble polymer and amphipathic polymer and (b) a process of polymerizing the mixed pre-mixed solution by heating or exposing to light.

By said polymerization reaction, the water-soluble crosslinkable polymer matrix is formed and said gel adhesive compositions are obtained. In addition, in said pre-mixed solution, depending on the desired performance of said gel adhesive compositions, said moisturizer can further be contained in 50% to 80% by weight with respect to the amount excluding water from the total amount of the gel adhesive compositions and water-insoluble polymer having adhesiveness can also be contained. In addition, said gel adhesive compositions also can be obtained by heating or exposing to light within the pH range of said pre-mixed solution of 4 to 7. In other words, in said process (a), it is preferable that the manufacturing method of gel adhesive compositions include the process of regulating said pre-mixed solution to pH 4 to 7.

Originally, water-soluble acrylic ester or acrylamide derivative, stored in alkaline aqueous solution, whether it is monomer or polymer, hydrolysis of ester group or of amide group progresses. On the other hand, when the pH gets too acidic, hydrolysis progresses likewise. Therefore, by adjusting the pH to between 4 and 7, inhibition of hydrolysis of acrylic monomer is available and together with the storage property of pre-mixed solution, storage stability for a long term after generation of a gel is improved.

By adding a certain amount of mineral acid or organic acid to said pre-mixed solution, the pH can be adjusted to between 4 and 7. In this case, it is preferable to use multifunctional mineral acid or (and) organic acid. Further, it is preferable to use these multifunctional acids and salts thereof in combination since the pH buffering property appears and the pH can be further stabilized. Examples of multifunctional acids include mineral acid such as sulfuric acid, phosphoric acid, carbonic acid, and the like. Further, organic acids include multifunctional carbonic acid such as citric acid, oxalic acid, malonic acid, succinate acid, tartaric acid, and the like. Regarding said mineral acid, said organic acid, and salts thereof, the added amount with respect to the pre-mixed solution is not specifically limited and depending on the capability of the pH regulators, it can be added.

Amphipathic Polymer

The gel adhesive compositions of the present invention demonstrate good adhesion to a surface of polyethylene terephthalate film since said gel adhesive compositions include amphipathic copolymer, and further, it demonstrates good adhesion to a carbon coated surface which is an electrode element portion which was formed by a paste mainly composed of polyester or polyurethane resin including graphite. Further, when the gel adhesive compositions of the present invention include amphipathic polymer as well as water-insoluble adhesive polymer, since dispersal stability of said water-insoluble polymer improves particularly during preparation of said pre-mixed solution, gel adhesive compositions with uniform and high quality stability can be obtained.

Amphipathic polymers include copolymers of hydrophilic monomers and hydrophobic monomers such as vinyl pyrrolidone/vinyl acetate copolymer, vinyl pyrrolidone/acrylic acid alkyl copolymer, low saponification polyvinyl alcohol, and the like. As said amphipathic polymers, although a high molecular polymer having amphipathic properties exists without copolymerization, copolymers are more preferable since there are some practical advantages, for example, by changing copolymerization ratio, hydrophilic group and hydrophobic group can be adjusted and the like. In addition, the ratio of hydrophilic group and hydrophobic group in the copolymer most preferably is between 1:1 and 3:1 by mole ratio.

Amphipathic property in the present invention means solubility in at least mixed solvents of organic solvents and water, and preferably solubility in both water and polar organic solvents. Examples of mixed solvents of organic solvents and water include mixed solvents of ethanol and water in the ratio of 60:40. Therefore, said amphipathic polymer refers to a polymer which is soluble in mixed solvent of ethanol and water in the ratio of 60:40 at room temperature.

Among said amphipathic polymers, polyvinyl alcohol with a saponification degree of 50% to 75% particularly is preferable. When the saponification degree is less than 50%, water solution gets difficult though not impossible and the handling properties during production decreases. In addition, when the saponification degree exceeds 75%, while water-solubility increases, salting out is likely to occur and when much ionic additives such as electrolyte and the like is used, sometimes it is not suitable. In addition, regarding the degree of saponification of the polyvinyl alcohol, a saponification degree of 98% or more is called complete saponification, a saponification degree of 80% to 98% is called partial saponification, and a saponification degree of not greater than 80% is called low saponification. Regarding partial saponification, when classified in more detail, a saponification degree of around 95% sometimes is called middle saponification and a saponification degree of 80% to 95% sometimes is called partial saponification. Further, the percentage of saponification is calculated by the following formula:

Saponification degree=polyvinyl alcohol unit/(vinyl acetate unit+polyvinyl alcohol unit)×100

※ calculated by substituting the amount of substance (number of moles) of each unit in the above formula.

Specific examples of said amphipathic polymer include vinyl pyrrolidone/vinyl acetate copolymer such as trade names "RUBISCOL VA73 W" (copolymerization mole ratio: vinyl pyrrolidone/vinyl acetate=7/3), "RUBISCOL VA64 W" (copolymerization mole ratio: vinyl pyrrolidone/vinyl acetate=6/4) sold by BASF Japan Ltd., and the like. Further, as low saponification polyvinyl alcohol, trade name "J POVAL JMR-10M" (saponification degree 65%) manufactured by Japan Vam & Poval Co., Ltd., trade name "GOSEFIMER LW-300" (saponification degree 53 to 60%) manufactured by The Nippon Synthetic Chemical Industry Co., Ltd., and trade name "DENKAPOVAL MP-10" (saponification degree 70%) manufactured by Denki Kagaku Kogyo Kabushiki Kaisha and the like are exemplary.

Although the amount of said amphipathic polymer to be used is not specifically limited, in order to obtain improved dispersal stability of pre-mixed solution by addition, it is preferable that the content to be added is not less than 0.05% by weight with respect to the amount excluding water from the total amount of said gel adhesive compositions, and further preferably not less than 0.1% by weight. Further, when the amount to be added is too much, since the viscosity of the pre-mixed solution increases, it takes time to vent the air bubbles which get mixed during the compounding process, or when the amount of the electrolyte to be added is large, water-insoluble polymers are liable to be coagulated. Therefore, it is preferable that the amount of said amphipathic polymer is not greater than 7.0% by weight with respect to the amount excluding water from the total amount of said gel adhesive compositions, and further preferably not greater than 4.0% by weight. In addition, in order to improve dispersal stability, such additional amount is enough for good effect.

Electrolyte

When used as conductive adhesives for electrodes for measuring bio electric potentials including the usage for electrocardiogram (ECG), brain wave, nystagmus, electromygram and the like, electrodes for electric stimulation used for TENS, low-frequency therapy, and the like, and electrodes for dispersive electrodes for electric scalpels and for electrodes for iontophoresis and the like, the conductive properties can be enhanced by adding an electrolyte salt. As electrolyte salt, it is preferable to use a chloride salt of an alkaline metal or an alkaline earth metal.

As a preferable electrolyte salt, chloride salt of lithium, sodium, potassium, magnesium, calcium, and the like are exemplary. Any one of these or some of these may be used.

When the electrolyte salt is added with a purpose of providing conductivity, the content amount preferably is not less than 0.5% by weight with respect to the amount excluding water from the total amount of said gel adhesive compositions. Further, as more electrolyte is added, conductivity is improved. However, when the amount is too much, water-insoluble polymers are more likely to coagulate and when the amount to be added exceeds some specific amount, the disadvantages of said coagulation or lengthening of time for solution at the preparation process of pre-mixed solution exceeds the advantages of improved conductivity, and therefore, it is preferable that the amount to be added is not greater than 6.0% by weight with respect to the amount excluding water from the total amount of said gel adhesive compositions, and more preferably, not greater than 4.0% by weight.

Surfactant

In manufacturing the gel adhesive compositions of the present invention, since coagulation tendency caused by salting out of water-insoluble polymers or of copolymer of amphipathic copolymers can be reduced by adding surfactants to the pre-mixed solution, it is possible to increase the amount of the pH buffering agent to be added. In particular, surfactants having polyoxyethylene alkyl ether with sulfuric ester group are preferable. As preferable examples, such surfactants as having structures of (formula 1) to (formula 6) are exemplified.

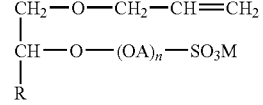

Formula 1

-continued

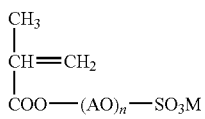
Formula 2

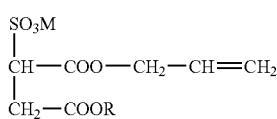
Formula 3

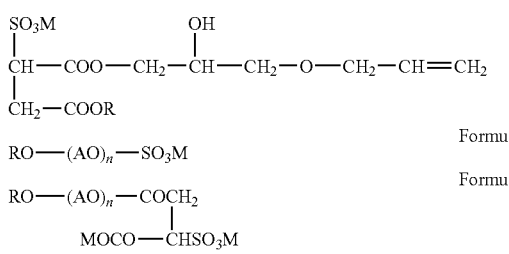
Formula 4

RO—(AO)$_n$—SO$_3$M
Formula 5

RO—(AO)$_n$—COCH$_2$
         |
    MOCO—CHSO$_3$M
Formula 6

In the formulas, R represents an alkyl group, M represents an ammonium salt or an alkaline metal salt, AO represents alkylene oxide (ethylene oxide or propylene oxide), and n represents an integer from 1 to 50.

As examples of having the structure of formula 1, AQUARON KH-05 and KH-10 (manufactured by Daiichi Kogyo can be exemplified, as examples of having the structure of formula 2, ELEMINOL RS-30 (manufactured by Sanyo Chemical Industries, Ltd) can be exemplified, as examples of having the structure of formula 3 ELEMINOL JS-2 (manufactured by Sanyo Chemical Industries, Ltd) can be exemplified, as examples of having the structure of formula 4, LATEMUL S-180 A, S-180 (manufactured by Kao Corporation) can be exemplified, as examples of having the structure of formula 5, EMAL D-3-D, LATEMUL E-118-B, E-150, LEVENOL WX (manufactured by Kao Corporation), HITENOL 08E, 18E, LA series (manufactured by Daiichi Kogyo) can be exemplified, and as examples of having the structure of formula 6, NEWCOL 293, RA544 (manufactured by Nippon Nyukazai Co., Ltd), and the like are exemplary.

In order to obtain an effect by the addition of these surfactants, it is preferable to add not less than 0.1% by weight with respect to the pre-mixed solution and when effects of the adhesiveness and other performances are taken into consideration, it is preferable to add not greater than 2.0% by weight with respect to the pre-mixed solution. The method of adding the surfactants is not specifically limited.

Peroxide

In manufacturing the gel adhesive compositions of the present invention, by adding at least 0.003% by weight of peroxide to the pre-mixed solution, prevention of yellowing of the gel after polymerization is possible. On the contrary, even when peroxide is added over 0.3% by weight to the pre-mixed solution, no big difference appears in preventing yellowing of the gel and moreover, the content of peroxide which remains in the gel increases and, for example, when used as biomedical electrodes, there is high risk of decaying the elements. The amount of peroxide which remains in the gel decreases by maturing it for a certain period of time after the generation of the gel. Maturing means to leave the gel under a certain specific temperature to promote the decomposition of said peroxide and the like. In order to promote the decomposition of said peroxide, it is preferable to set the maturation temperature not less than 30° C. Further, when the maturation temperature is too high, there is the risk that the gel matrix and the like are decomposed or deteriorated as well as the risk that the protection film and the like adhered to the gel may start contracting, wrinkling, or deforming and therefore, it is preferable to set the temperature not greater than 60° C. The most preferable maturing temperature is 35 to 45° C.

As said peroxide, hydrogen peroxide, percarbonate soda, sodium perborate, peracetic acid, chlorine dioxide, and the like are exemplary. It is preferable that these peroxides are diluted up to not greater than 10% by water and then added to the pre-mixed solution. Further, once they are added to the pre-mixed solution, the pre-mixed solution should be used within 24 hours. When a long period of time passes after these peroxides are added, a polymerization reaction starts and there is a possibility that the gel will be generated unintentionally.

(Manufacturing Method of the Present Invention)

The present invention also pertains to a manufacturing method of gel adhesive compositions, the method comprising the steps of mixing pre-mixed solution that includes a monomer and a crosslinkable monomer for forming a matrix of water-soluble polymer, a moisturizer, water, a water-insoluble polymer and amphipathic polymer, and copolymerizing this mixed pre-mixed solution by heating or radiating.

The method of manufacturing the gel adhesive composition of the invention is, as described above, a manufacturing method of the gel adhesive composition comprising the following steps: (a) mixing a pre-mixed solution containing a non crosslinkable monomer, a crosslinkable monomer, a moisturizer, water, a water-insoluble polymer, and an amphipathic polymer and (b) carrying out polymerization by heating or radiating light to the mixed pre-mixed solution. More particularly, the method is preferable to comprise the following steps.

(1) Preparation of Pre-Mixed Solution (i) Water-insoluble polymer emulsion is added to a solution evenly stirred after diluting amphipathic polymer which was dissolved in water beforehand by water as required, and is evenly dispersed. Next, a moisturizer is put and is stirred until evenly dispersed. This is named (liquid 1). In addition, when amphipathic polymer is dissolved in water beforehand, the amount can be set appropriately based on the compounding amount in preparing (liquid 1).

(ii) A monomer is put into (liquid 1) and is stirred. Because heat absorption or heat generation may occur depending on the kinds of monomers during dissolution, it is preferable to warm in the case of heat absorption and to cool in the case of heat generation. When warming or cooling, it is preferable to set the temperature of (liquid 1) within the range of 10° C. to 50° C. and more preferably, within the range of 20° C. to 40° C. When the temperature is too low, it takes time for monomer solution particularly when monomer is in a solid state and also it takes time for dissolving other components to be added than a monomer. Depending on the components to be added, when the temperature is too low, sometimes they are not soluble. Further, when the temperature decreases extremely, the emulsion or other polymer components sometimes coagulate. In addition, when the temperature is too high, likewise, poor dispersion of the emulsion occurs and when the highly reactive component is included, reaction starts or causes runaway, and further, volatile components in a composition liquid vaporizes and component liquid as previously set may not be obtained.

(iii) When an electrolyte is required, it is preferable to put it after the process of (ii). When the electrolyte is put in, by salting out, sometimes emulsion and other polymer components may get coagulated, however, by dissolving a monomer earlier, the effect of inhibiting coagulation is obtained. Although a monomer is in itself inferred to act as surfactants, the detailed structure is unknown.

(iv) Next, needed components and a polymerization initiator other than those described above are added and stirred and mixed until all of the components are completely dissolved to obtain a pre-mixed solution. The above-mentioned amphipathic polymer is added preferably in an amount of 0.05 to 7.0% by weight with respect to the total amount of the pre-mixed solution except water. Also, in the case that the surfactant is added to the pre-mixed solution, the surfactant is preferable to be added properly to the pre-mixed solution to be in an amount of 0.1 to 2.0% by weight in the pre-mixed solution. Further, the above-mentioned peroxide is preferable to be added further in an amount of 0.003 to 0.3% by weight to the mixed pre-mixed solution and then mixed and dissolved before polymerization. The water-insoluble polymer is preferably an emulsion using water as a dispersant.

In the case that the pre-mixed solution contains both of the water-insoluble polymer and the amphipathic polymer, such a pre-mixed solution can be used as a pre-mixed solution for a gel adhesive composition with stabilized dispersion. That is, it is a pre-mixed solution for a gel adhesive composition containing a non crosslinkable monomer, a crosslinkable monomer, a moisturizer, water, a water-insoluble polymer, and an amphipathic polymer and in which the amphipathic polymer is contained in an amount of 0.05 to 7.0% by weight with respect to the total amount of the pre-mixed solution except water. In the invention, the pre-mixed solution for the gel adhesive composition is more preferable to contain the water-insoluble polymer in an amount of 3 to 20% by weight with respect to the total amount of the composition except water.

(2) Storage of Pre-Mixed Solution

Regarding storage of pre-mixed solution, although it is not specifically limited as long as emulsion or other components to be added are stable, it is preferable to store the pre-mixed solution within a temperature range of 0° C. to 50° C. and further preferably within a temperature range of 5° C. to 40° C.

(3) Generation of a Gel

A gel comprising a gel adhesive composition with specific thickness is obtained by allowing pre-mixed solution to drip onto a resin film and the like (base film) and on its top surface, a resin film and the like (top film) with release treatment is covered and pushes the liquid to spread out, followed by polymerizing and cross-linking pre-mixed solution by exposing to heat or light (ultraviolet ray) in a state where the liquid is controlled to have specific thickness. As base films, polyester, polyolefin, polystyrene, paper or a paper in which a resin film is laminated, and the like can be used.

When a base film is used as a release substrate, the ones with release treatment conducted on a surface of polyester, polyolefin, polystyrene, paper or a paper in which a resin film is laminated and the like can preferably be used. In particular, biaxially-stretched PET films or OPP and the like are preferable. As a method for release treatment, silicone coatings can be exemplified. In particular, thermosetting silicone coatings by which cross linking and curing reaction is conducted with heat or ultraviolet ray are preferable.

When the base film is used not as a release substrate but as a backing material for adhesives, resin films of polyester, polyolefin, polystyrene, polyurethane, and the like are used without release treatment. In particular, polyurethane is preferable since it is flexible and there exist some which have water vapor transmitting property. Since polyurethane usually is too soft alone and therefore difficult to handle during the production process, polyolefin, paper, or the like are laminated as carriers. It is necessary to use in the gel generation process with these carriers.

As top films, basically the same materials as in base films can be used, but when the gel is generated by light radiating, it is necessary to select materials which do not shield the light. Further, it is better that films used for said backing should not be used as top films. In particular, when the deterioration is likely to occur by exposing to the light such as ultraviolet rays and the like, it is further not preferable since the film is put in the position to which ultraviolet rays directly exposes.

When the gel is polymerized and cross-linked consecutively and the generated gel of a gel adhesive composition is wound in a roll state, flexibility is required either for base films or top films. When non-flexible film is used on both surfaces, there is a high risk of winding wrinkle generation. Although flexible film can be used either for inner surface or outer surface of a roll, it is preferable to place it outside.

In the gel adhesive composition of the present invention, when shaped into a sheet, as required, it is possible to embed a non-woven cloth or a woven cloth as reinforcing materials. These reinforcing materials are used for reinforcing the gel and improving the shape keeping ability of the gel at the time of cutting. These reinforcing materials are required for example, for simplifying the handling of end processors when the gel adhesive compositions are distributed as reinforcing materials for processing. Useful non-woven cloth or woven cloth materials include natural fabrics such as cellulose, silk, linen, and the like; synthetic fabric such as polyester, nylon, rayon, polyethylene, polypropylene, polyurethane, and the like; blend thereof; and, further, as required, binders are used, and further more, sometimes they are colored.

When the gel adhesive composition of the present invention contains amphipathic polymer as well in addition to non crosslinkable monomer of water-soluble polymer, cross linkable monomer, moisturizer, water, and water-insoluble polymer having adhesiveness, in a pre-mixed solution including these, dispersal stability of said water-insoluble polymer becomes good. For this reason, storage of monomer-mixed solution is easy since stirring is not required. Further, the process from preparing said pre-mixed solution to forming a gel on the base film does not have to be done consecutively. In addition, it is preferable in the manufacturing method of the gel adhesive compositions of the present invention to use each component of a pH regulator, water-soluble polymer, amphipathic polymer, a surfactant, and peroxide in the above composition and/or the above additional amount so that each component can show the desirable effect as explained in each section above.

In the gel adhesive composition of the present invention, hydrophilic polymer may be included as tackifier so that the dispersibility of an emulsion in the pre-mixed solution stage is not deteriorated. For example, polyacrylic acid and salts thereof, polyvinyl pyrrolidone, polyvinyl alcohol (which is not amphipathic), polyethylene oxide, and the like can be used. In addition, as tackifier of an emulsion, rosin series resin may be added.

In the gel adhesive composition of the present invention, as required, antiseptics, disinfectants, mildew proofing agents, corrosion inhibitors, antioxidants, stabilizers, perfumes, colorants, and the like and further, anti-inflammatory agents, vitamin preparations, whitening agents, and other medical component may be added appropriately.

In addition, from the above, as a preferable embodiment of the invention, the following gel adhesive compositions can be exemplified. That is, a gel adhesive composition containing a crosslinked water-soluble polymer, water, a moisturizer, an amphipathic polymer, a water-insoluble polymer having adhesiveness, and an electrolytic salt and which contains water 13 to 40% by weight, and the crosslinked water-soluble polymer 15 to 35% by weight, the water-insoluble polymer 3 to 20% by weight, the amphipathic polymer 0.05 to 7.0% by weight, the moisturizer 50 to 80% by weight, and the electrolytic salt 0.5 to 6.0% by weight with respect to the total amount of the composition except water.

(Electrodes)

The invention is an electrode comprising a gel adhesive layer which contains the gel adhesive composition. The gel adhesive composition is preferably a composition containing a crosslinked water-soluble polymer, water, a moisturizer, and an amphipathic polymer and in which the amphipathic polymer is contained in an amount of 0.05 to 7.0% by weight with respect to the total amount of the composition except water. The gel adhesive layer can be stuck excellent even to the surface of a polyethylene terephthalate layer and has an excellent sticking property even to a carbon coat layer formed from a carbon paste containing polyester type or polyurethane type resin as a binder. Therefore, the electrode can be an electrode comprising the gel adhesive layer having an interface with a carbon coat layer and another interface with a polyethylene terephthalate layer by giving the conductivity to the gel adhesive layer by a conventional method such as impregnation of an electrolytic substance or the like. For example, the following electrode can be employed. That is, the electrode comprises a polyethylene terephthalate layer composing a sheet-like surface substrate; a pair of carbon coat layers arranged in the rear face of the polyethylene terephthalate layer at an interval and connected to a pair of electrode terminals, respectively, and composing an electrode element part; and gel adhesive layers respectively stretched over the rear faces of the pair of the carbon coat layers and the rear face of the polyethylene terephthalate layer positioned between the pair of the carbon coat layers and in which the gel adhesive layers contain the gel adhesive composition which contains a crosslinked water-soluble polymer, water, a moisturizer, and an amphipathic polymer which is contained in an amount of 0.05 to 7.0% by weight with respect to the total amount of the composition except water.

In the case of the electrode comprising the gel adhesive layers containing the gel adhesive composition, since the gel adhesive layer is stuck excellently to both of the carbon coat layer and the polyethylene terephthalate layer and thus has a good sticking property even to the skin face of a human body without causing interlayer separation from both layers. Therefore, the electrode of the present invention can preferably be used for the electrode for measuring electrocardiogram, for low-frequency therapy, and for measuring a body fat ratio. Further, the electrode of the present invention can show excellent adhesiveness by containing water-insoluble polymer.

FIG. 1 is a drawing which shows the first embodiment example of the electrodes of the present invention. Said embodiment example is an embodiment example of the electrodes in which said gel adhesive layer has an interface with a carbon coat layer and further has an interface with a polyethylene terephthalate layer. FIG. 1(a) is a drawing showing a surface of electrodes of the present invention. FIG. 1(b) is a sectional view taken along the line A-A in electrodes of FIG. 1(a). FIG. 1(c) is a drawing showing a back surface of electrodes of FIG. 1(a).

As shown in FIG. 1(a), in electrode 1 of the present invention, a pair of electrode terminals 2 is provided. Said electrode terminals 2, as shown in FIG. 1(b) are provided on a specific position of electrode 1 by intruding to connecting device 3 with interposing surface material 4 which is a polyethylene terephthalate layer and carbon coat layer 5 therebetween. In connecting device 3, the portion appearing on carbon coat layer 5 which functions as an electrode is coated with insulation tape 7. Further, gel adhesive layer 6 is formed in a way that an interface between said gel adhesive layer and said carbon coat layer and an interface between said gel adhesive layer and polyethylene terephthalate layer exist on one surface of said gel adhesive layer. As mentioned above, in electrode 1, gel adhesive layer 6 is formed and on the opposite surface of surface material 4, separator 8 is formed. At the time of using said electrode, separator 8 is peeled off and a surface of gel adhesive layer 6 is adhered to a skin surface of a human body.

Although said electrodes have a laminated structure as mentioned above, in a laminated structure of surface material 4 and carbon coat layer 5, as shown in FIG. 1(c), they have a pattern in which PET region is sandwiched between two carbon coat regions. However, since in the electrodes of the present invention, gel adhesive compositions which are included in a gel adhesive layer shows good adhesion to both polyethylene terephthalate surface and carbon coat surface, when peeled off from a skin surface, delamination between substrate sheet layer and conductive gel adhesive layer is not generated and so, the electrodes can preferably be used for electrodes for measuring electrocardiogram, electrodes for low-frequency therapy, electrodes for measuring a body fat ratio and the like.

Further, since the electrodes of the present invention are excellent in adhesion, they can preferably be used for electrodes with other shapes. FIGS. 2(a) to 2(d) are sectional views in the vicinity of electrode terminals regarding the second to fifth embodiment examples of the electrodes of the present invention. Further, FIG. 3 is a lateral view of the sixth embodiment example of the electrodes of the present invention and a front view in the side of a gel adhesive layer.

Figure 2:
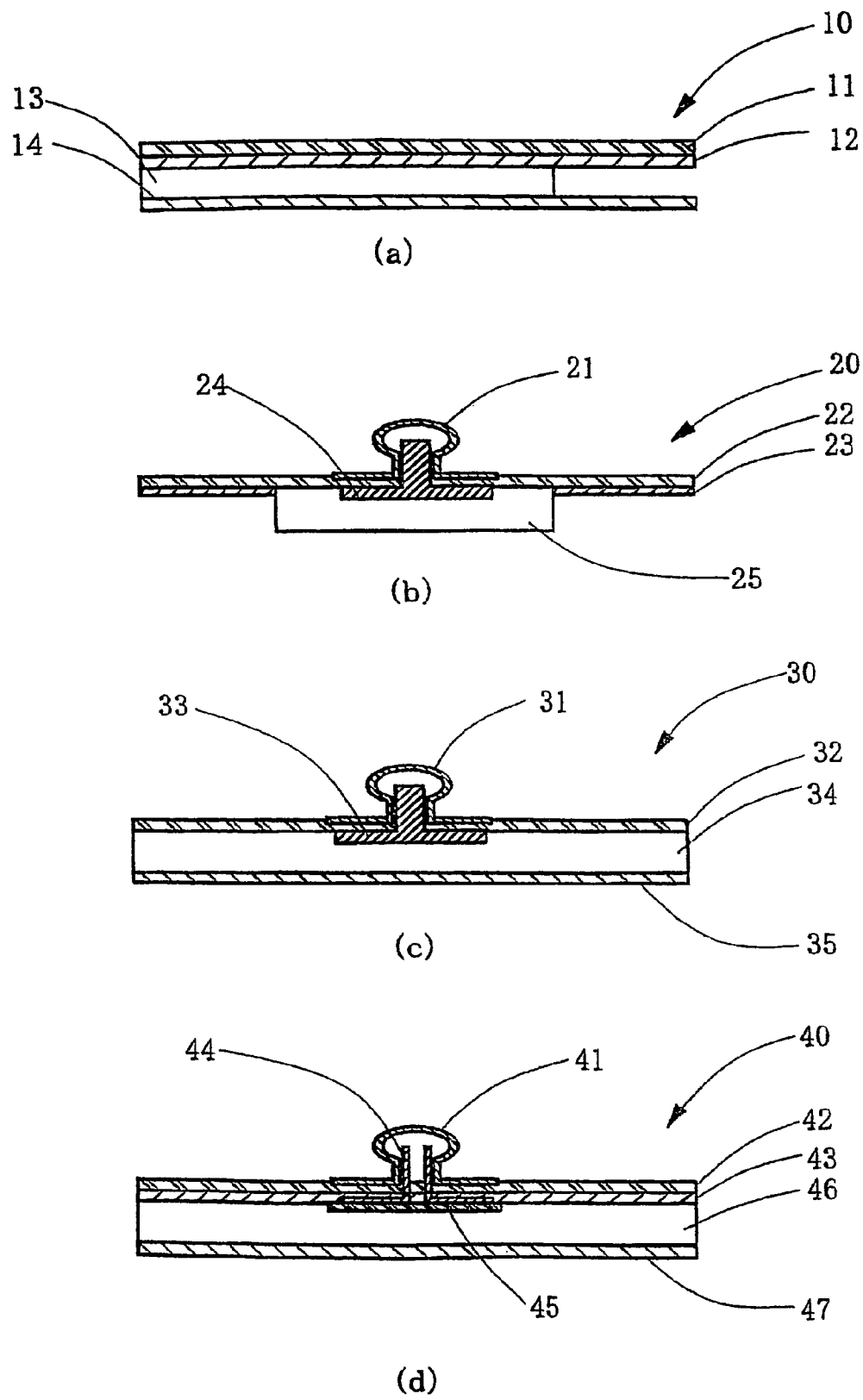
FIG. 2(a) to 2(d) are cross-sectional views in the vicinity of the electrode terminals of the second to the fifth embodiments of the electrodes of the invention.
Figure 3:
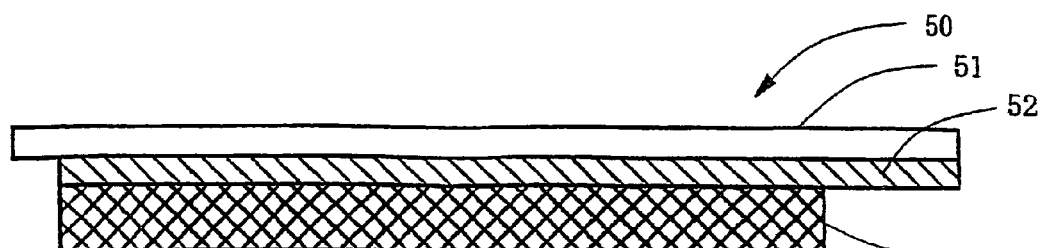
FIG. 3 is a drawing showing an electrode of the sixth embodiment using a gel adhesive composition according to the present invention.
Figure 3:
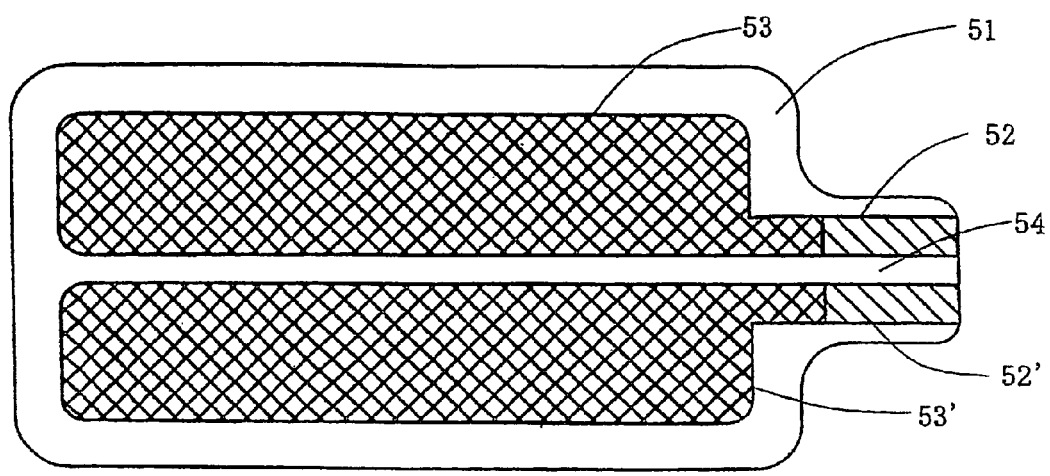
Figure 3:
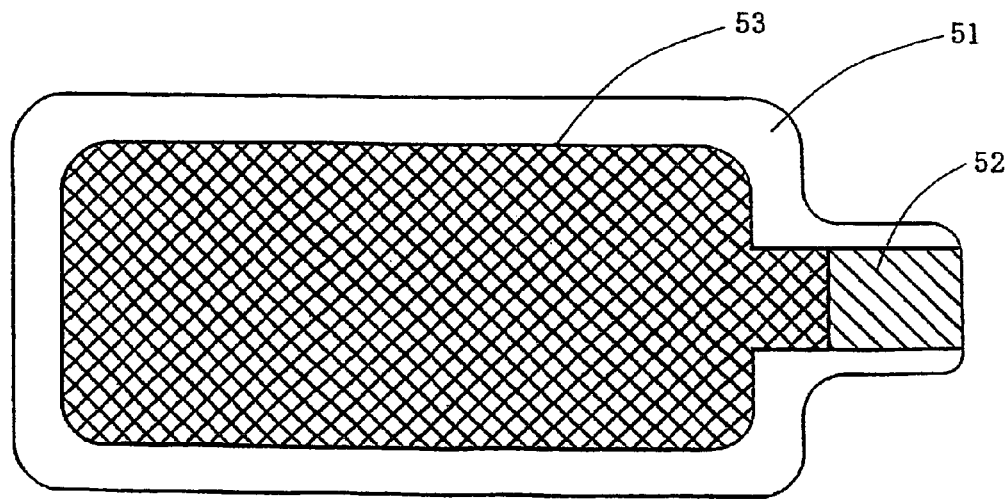

FIG. 2(a) is a sectional view of the second embodiment example of the electrodes of the present invention. The electrodes of the embodiment examples can preferably be used for electrodes for electrocardiogram examination and the like.

In electrode 10, conductive layer 12 is formed by printing and coating conductive inks which comprises metals such as Ag, Ag/Ag Cl and the like and carbon and the like on a resin film which is surface material 11 or conductive layer 12 is formed by laminating conductive film in which metal foils (aluminum, stainless, Ag and the like) or carbon and the like are kneaded on a resin film which is surface material 11, thereby forming a one-side conductive film provided with a conductive layer on one side. Electrode 10 is a simple electrode simply composed of putting above mentioned gel adhesive compositions on conductive layer 12 and with gel adhesive layer 13 simply formed on one side of a conductive film. At the time when electrode 10 is used, separator 14 formed on gal adhesive layer 13 for protecting a gel surface is peeled off and the portion on which no gel of a one-side conductive film is formed is connected to a lead wire pinched by alligator clips and the like. Thus, electrode 10 is used as an electrode in which a gel adhesive layer surface appearing with the delamination of separator 14 is attached on skin surfaces of a human body and the like.

It is preferable that the thickness of a resin film as surface material 11 is about 5 to 150 μm. Although the materials of said resin film are not specifically limited, synthetic paper suitable for printing (the one prepared by adding inorganic fillers to polypropylene), PET, OPP film and the like are preferable. In addition, in order to enhance appearance, decorative printing may be conducted to a surface which is opposite to a coating surface of a conductive ink on a surface material, or in order not to damage flexibility, paper, non-woven cloth, a foam body (a flexible foam sheet such as polyethylene, polyethylene vinyl acetate, polyurethane and the like), films of polyurethane and the like or sheets thereof may be laminated. Although as conductive inks, publicly known conductive ink can be used, multiple layered coating by combinations of several kinds thereof may be available.

FIG. 2(b) is a sectional view of the third embodiment example of electrodes of the present invention. Electrodes of the present embodiment example can preferably be used for electrodes of electrocardiogram for general use or operating rooms and the like.

Electrode 20 is an electrode having a combination of an electrode element with a pinching structure of snap terminal 21 and element 24 and a gel as a basic electrode structure. The area of surface material 22 is larger than that of gel adhesive layer 25 and adhesives are coated on a portion which goes over and adhesive treatment surface 23 is formed there. Electrode 20 is provided with a structure in which adhesive treatment surface 23 as framed adhesive portion is provided since adhesiveness of a gel included in gel adhesive layer 25 is not satisfactory when the gel is used alone. As electrode element 24, a resin mold product on which metals such as Ag/Ag Cl and the like are coated can be used. As snap terminal 21, although publicly known terminals having conductivity can be used, snap terminals are either metals such as stainless and the like or resin mold products in which carbon is kneaded. As surface material 22, non-woven cloth, foam body (flexible foam sheet including polyethylene, polyethylene vinyl acetate, polyurethane, and the like) polyurethane, PET, PVC and the like can be used. These surface materials can be used alone or in combinations of two or more of them. Usually, the ones with adhesive treatment applied on one surface of these surface materials are used. Electrode 20 is excellent in adhesiveness since it employs the above mentioned gel adhesive compositions, its adhesion as well as adhesion treatment surface adhere to a surface of human body skin and the like. In addition, although a separator is not shown in FIG. 2(b), when an electrode is used, as in the already mentioned second embodiment example, separator is peeled off and used.

FIG. 2(c) is a sectional view which shows the fourth embodiment example in an electrode of the present invention. The electrode of the present embodiment can preferably be used as an electrode for electrocardiogram for general purposes or for infants.

Electrode 30 is an electrode having a pinching structure of snap terminal 31 and element 33 as in the above mentioned third embodiment example. Gel adhesive layer 34 is formed on a whole surface of surface material 32 and on the opposite surface of surface material 32 in gel adhesive layer 35, separator 35 is formed. Although basically electrode 30 has the same structure as electrode 20, electrode 30 has no framed adhesive portion and it adheres to a skin only with the adhesion of a gel. Since a whole surface is a gel, skin irritation is not likely to occur. Although surface material 32 can be used as in electrode structure 2, surface material used in the present structure does not require adhesion treatment.

FIG. 2(d) is a sectional view of the fifth embodiment example of an electrode in the present invention. Electrodes of the present embodiment example can preferably be used as electrodes for electric therapy, TENS, EMS, iontophoresis and the like.

In electrode 40, on a whole surface of surface material 42, a conductive ink is coated as in the above mentioned second embodiment example and electrode layer 43 is formed. Metal snap is employed for snap terminal 41 and in order to fix a snap, it is caulked with a metal eyelet 44. When an eyelet 44 which is a metal and gel directly contact with each other, since electricity gets centered on eyelet portion, insulation tape 45 is provided and also gel adhesive layer 46 is provided on conductive layer 43 and on eyelet 44 so that an eyelet and gel might not contact directly with each other. As surface material 42, the same kinds as used in above mentioned second embodiment example can be used. Although metals are used for snap terminals and eyelets respectively, in order to avoid corrosion, stainless is preferable and for example, SUS 316 L and the like having both less corrosive property and intensity is exemplified. As insulation tapes, resin films with adhesion treatment on one side surface are used. In addition, in electrode 40, separator 47 is formed on the opposite surface of surface material 43 in gel adhesive layer 46 and as in the above mentioned embodiment example, it is used by being peeled off at the time when the electrode is used.

FIG. 3 is a view which shows the sixth embodiment example of an electrode of the present invention. Electrode of the present embodiment example can preferably be used for grounding pads of electric scalpels (dispersive electrodes) and the like.

FIG. 3(a) is a lateral view of electrode 50 which is the sixth embodiment example. Electrode 50 has a structure in which a surface material is further attached on a surface material of one side of electrode film in a structure of the second embodiment example in FIG. 2(a). On surface material 51 which is a surface material of the uppermost layer, conductive film layer 52 including a surface material is formed, and gel adhesive layer 53 is formed on conductive film layer 52. Between surface material 51 and conductive film layer 52, adhesion treatment is applied. Conductive film layer 52 is laminated with surface material 51 so that a conductive layer is on the side of gel adhesive layer 53. In electrode 50, gel adhesive layer 53 which includes above mentioned gel adhesive compositions is formed and adheres firmly to a skin.

In conductive film layer 52, only to one side surface of surface material conductive treatment is applied and has the same structure as in the laminated structure of surface material 11 and conductive layer 12 in the second embodiment example in FIG. 2(a). Although the structure of conductive film layer 52 conforms to electrode structure 11, when it is used as grounding pads of electric scalpels, since application of the high frequency current is required without disruption, it is preferable to laminate metal foil which has highly electric conductive property on a resin film. As metal foils, metal foils of such as aluminum, stainless, copper, nickel, and the like can be used. Among them, aluminum foil is particularly preferable since it is flexible and has high electric conductivity and is less likely to corrode. As surface material 51 of the present structure, non-woven cloth, foam body (flexible foam sheet such as polyethylene, polyethylene vinyl acetate, polyurethane and the like) can be used.

Further, regarding electrode 50 shown in FIG. 3(a), two patterns can be employed which are the first pattern shown in FIG. 3(b) and the second pattern shown in FIG. 3(c). In the pattern of FIG. 3(b), conductive film layer 52 and conductive film layer 52', and gel adhesive layer 53 and gel adhesive layer 53' are in the state of insulation interposing insulation groove 54 therebetween. Dispersive electrodes for scalpels are used together with electric scalpel devices and active electrodes and many of said dispersive electrodes for scalpels have a circuit built in the electric scalpel devices for monitoring a contact state since a part of a dispersive electrode for scalpels is peeled off and when the contact area decreases, burn injury occurs. Generally, the device is so designed that by monitoring the value of resistance between insulated two electrode portions (in the embodiment, they correspond to 52 and 53, and, 52' and 53'), burn injury is prevented by cutting the output of the devices automatically when the value of resistance changes exceeding the preset value, caused by delamination and the like. Thus, by using the present embodiment, such a circuit as monitoring said contact state can be used.

EXAMPLES (Preparation of PVA Solution)

The amphipathic polymers, 20% aqueous solution of PVA having low saponification degree (commercially available as JMR-10M (saponification degree 65%) from Japan Vam & Poval Co., Ltd.) (PVA solution 1) and 20% aqueous solution of vinyl pyrrolidone/vinyl acetate copolymer (commercially available as Luviscol VA73 a molar ratio of vinyl pyrrolidone: vinyl acetate of 7:3 from BASF Japan, Ltd.) (VA solution) were first prepared.

Examples 1 and 2

Using a stirring/mixing apparatus in which temperature is controlled within the range of 30° C. to 40° C., A1 parts by weight of PVA solution 1 and B parts by weight of ion exchange water were mixed followed by stirring and dissolving until they uniform, further followed by adding D parts by weight of glycerin as a moisturizer and stirring until likewise uniform. Next, to said apparatus, E parts by weight of acryl amide as a monomer was added and, after stirring for some minutes, F parts by weight of sodium chloride as electrolyte was added thereto and as crosslinkable monomer, G parts by weight of polyethylene glycol dimethacrylate (BLENMER PDE-400: NOF Corporation) was added and was stirred until completely dissolved. To 100 parts by weight of obtained mixture liquid 3, as polymerization initiator, 0.15 parts by weight of 1-(4-(2-hydroxyetoxy)-phenyl)-2-hydroxy-2-methyl-1-propane-1-on (commercially available as IRGACURE 2959 from Ciba Specialty Chemicals) was added and milk-white monomer-mixed solution 4 was obtained. Obtained monomer-mixed solution 4 was dripped on a silicone coated PET film and it was covered by a silicone coated PET film from above and the liquid was uniformly pushed to spread uniformly and was fixed so that the thickness of the liquid became 0.5 mm. By irradiating with ultraviolet rays with energy of 3000 mJ/cm$^2$ thereto using a metal halide lamp, gel adhesive compositions of Examples 1 and 2 were obtained respectively having a thickness of 0.5 mm. The detailed compounding amount is shown in Table 1.

Examples 3 to 10, 12, and 13

Using a stirring/mixing apparatus in which temperature is controlled within the range of 30 to 40° C., A1 parts by weight of PVA solution 1 or A2 parts by weight of VA solution and B parts by weight of ion exchange water were mixed followed by stirring and dissolving until uniform, further followed by adding C1 parts by weight of emulsion of acrylic acid ester copolymer (solid content 50% by weight, trade name "POLYZOL PSA SE-1730", manufactured by Showa Polymer Co., Ltd.) or C2 parts by weight of emulsion of acrylic acid ester copolymer (solid content 50% by weight, trade name "VINYBLAN ADH-1048" manufactured by Nissin Chemical Industry Co., Ltd) or C3 parts by weight of emulsion of acrylic acid ester copolymer as a water insoluble polymer (solid content 60% by weight, trade name "VINYBLAN ADH-893 T", manufactured by Nissin Chemical Industry Co., Ltd) was added and was stirred until uniformly dispersed (it was judged as uniform when unevenness of white turbidity disappeared by visual observation). Next, D parts by weight of glycerin as a moisturizer was added and was stirred until likewise uniform. Next, E parts by weight of acryl amide as a monomer was added and after stirring for some minutes, F parts by weight of sodium chloride as electrolyte was added and as crosslinkable monomer, G parts by weight of polyethylene glycol dimethacrylate (trade name "BLENMER PDE-400" manufactured by NOF Corporation) was added and was stirred until completely dissolved. To 100 parts by weight of obtained mixture liquid 3, as polymerization initiator, 0.15 parts by weight of 1-[4-(2-hydroxyetoxy)-phenyl]-2-hydroxy-2-methyl-1-propane-1-on (commercially available as IRGACURE 2959 manufactured by Ciba Specialty Chemicals) was added and milk-white monomer-mixed solution 4 was obtained. The obtained monomer-mixed solution 4 was dripped on a silicone coated PET film and it was covered by a silicone coated PET film from the above and the liquid was pushed to spread and was fixed so that the thickness of the liquid became 0.5 mm. By irradiating with ultraviolet rays with energy of 3000 mJ/cm$^2$ thereto using a metal halide lamp, gel adhesive compositions were obtained having a thickness of 0.5 mm. The detailed compounding amount is shown in Tables 1 and 2.

Examples 11, and 14 to 18

H parts by weight of 20% citric acid aqueous solution, I parts by weight of 20% sodium citrate aqueous solution, and J parts by weight of 6% hydrogen peroxide solution were mixed and were added to monomer-mixed solution 4 and were stirred for 10 minutes until uniformly dissolved (monomer-mixed solution 5). The obtained monomer-mixed solution 5 was dripped on a silicone coated PET film and it was covered by a silicone coated PET film from the above likewise and the liquid was pushed to spread uniformly and was fixed so that the thickness of the liquid became 0.5 mm. By irradiating ultraviolet rays with energy of 3000 mJ/cm$^2$ thereto using a metal halide lamp, gel adhesive compositions were obtained having a thickness of 0.5 mm. The detailed compounding amount is shown in Tables 2 and 3.

Examples 19 and 20

H parts by weight of 20% citric acid aqueous solution, I parts by weight of 20% sodium citrate aqueous solution, and K parts by weight of polyoxyethylene alkyl ether sulfuric ester salt as a surfactant (trade name "AQUARON KH-10 manufactured by Daichi Kogyo Seiyaku Co., Ltd.) were added to monomer-mixed solution 4 and were stirred for 20 minutes until uniformly dissolved (monomer-mixed solution 6). The obtained monomer-mixed solution 6 was dripped on a silicone coated PET film and it was covered by the silicone coated PET film from the above likewise and the liquid was pushed to spread uniformly and was fixed so that the thickness of the liquid became 0.5 mm. By irradiating ultraviolet rays with energy of 3000 mJ/cm$^2$ thereto using a metal halide lamp, gel adhesive compositions were obtained having a thickness of 0.5 mm. The detailed compounding amount is shown in Table 3.

Comparative Examples 1 to 2

Using a stirring/mixing apparatus in which a temperature is controlled within the range of 30 to 40° C., D part by weight of glycerin as a moisturizer was added to B parts by weight of ion exchange water were mixed followed by adding E parts by weight of acryl amide as a monomer and was stirred for some minutes and further adding F parts by weight of sodium chloride as an electrolyte and G parts by weight of polyethyelen glycol diacrylate as crosslinkable monomer and was stirred until it got dissolved completely. To 100 parts by weight of obtained mixture liquid 3, as polymerization initiator, 0.2 parts by weight of 1-[4-(2-hydroxyetoxy)-phenyl]-2-hydroxy-2-methyl-1-propane-1-on (trade name "IRGA-CURE® 2959" manufactured by Ciba Specialty Chemicals) was added and colorless transparent monomer-mixed solution 4 was obtained. The obtained monomer-mixed solution 4 was dripped on a silicone coated PET film and it was covered by the silicone coated PET film from the above likewise and the liquid was pushed to spread and was fixed so that the thickness of the liquid became 0.5 mm. By irradiating ultraviolet rays with energy amount of 3000 mJ/cm$^2$ thereto using a metal halide lamp, gel adhesive compositions were obtained having a thickness of 0.5 mm. The detailed compounding amount is shown in Table 4.

Comparative Example 3

Monomer-mixed solution 4 was obtained by the same method as in Comparative Examples 1 to 2 except that C3 part by weight of emulsion of acrylic acid ester copolymer (trade name "VINYBLAN ADH-893 T", manufactured by Nissin Chemical Industry Co., Ltd) as water-insoluble polymer was added. Although the compounding order and method in manufacturing followed the Examples, when stirring was stopped, the separation of emulsion progressed and uniform gel could not be obtained. The detailed compounding amount is shown in Table 4.

Comparative Examples 4 to 5

Monomer-mixed solution 4 was attempted to obtain by the same method as in Comparative Examples 1 to 7 except that instead of amphipathic polymer copolymer, 20% aqueous solution of PVA of water-soluble polymer (trade name "JMR-10HH" (saponification degree 98.5%) (manufactured by Japan Vam & Poval Co Ltd.) or polyacrylic acid (trade name "AC-16H" manufactured by Nihon Junyaku Co., Ltd.) were used respectively, however, monomer-mixed solution 4 could not be obtained in both cases since both coagulated during stirring and gelated like a bavarois. The detailed compounding amount is shown in Table 4.

Comparative Example 6

Monomer-mixed solution 4 was attempted to obtain by the same method as in Example 3 except that instead of amphipathic copolymer, vinyl acetate copolymer emulsion (solid content 40%, trade name "VINYBLAN 1245L" manufactured by Nissin Chemical Industry Co., Ltd) was used, however, when stirring was stopped, separation of emulsion progressed and separation tendency was observed. Using monomer-mixed solution 4 within 1 hour after stopping stirring, with the same method as in Example 3, gel adhesive compositions with a thickness of 0.5 mm was obtained. The detailed compounding amount is shown in Table 4.

(Measurement of Adhesion)

The adhesion of gels obtained by Examples and Comparative Examples was measured.

Each one-side surface of the PET film of gel adhesives obtained by Examples 1 to 20 and Comparative Examples 1, 2, and 6 was peeled off and instead, synthetic paper on one surface with an inorganic filler coated was attached, followed by cutting 120 mm in length and 20 mm in width, thereby obtaining test strips.

A T type delamination test was conducted with a tensile testing machine after peeling off PET films remained on a gel surface of the obtained test strips and putting them on PFT films with a thickness of 38 μm and leaving for 30 minutes (tensile speed 300 mm). The results were shown in Tables 5 and 6. In addition, as PET films, PET films having a contact angle of 70 to 80 degrees with distilled water were used.

(Adhesion to Skin)

With the same way as in preparing the test strips used for measuring adhesion, regarding gel adhesive compositions obtained in Examples 1 to 20 and Comparative Examples 1, 2, and 6, test strips of 40 mm by 20 mm were prepared respectively for the number of subjects and the sensory evaluation was conducted by putting these gels to 6 subjects. As a test method, sensory evaluation was classified into 5 stages based on the following criteria regarding adhesion force to a skin by putting the test strips on the outer side of the arm, followed by peeling them off immediately. In addition, following sensation is obtained when approximately the following measurement value shown in parentheses below (peeling load 90 degrees) is applied.

5: feeling pain when peeled off from the skin (peeling load not less than about 450 g/20 mm)

4: adhering with satisfactory strength (peeling load not less than about 350 g/20 mm)

3: practically usable adhesive level (peeling load not less than about 250 g/20 mm)

2: adhering but adhesion force is rather weak (peeling load not greater than about 200 g/20 mm)

1: not available (peeling load not greater than about 100 g/20 mm)

Based on the above mentioned criteria, 6 persons evaluated skin adhesion by the average values of evaluating each sample. The results were shown in Tables 5 and 6.

(Compression Strength)

Gel adhesive compositions obtained by Examples 1 to 20 and Comparative Examples 1, 2, and 6 were respectively cut into 20 mm by 20 mm followed by attaching 6 sheets together thereby making test strips with a thickness of 3 mm. These test strips were set in a rheometer and 0.6 mm compression was applied at a speed of 300 mm/minute using stainless cylindrical measuring tool of 12 φ. The test was conducted for 3 test strips and compression stress was defined to be the average maximum stress of these. The measurement results are shown in Tables 5 and 6.

(Impedance Measurement)

Regarding gel adhesive compositions to which electrolyte was added obtained by Examples and Comparative Examples, the measurement of electric performance at the time of preparing electrodes was conducted. To electrode elements in which Ag/Ag Cl ink is coated by screen printing on one side surface of 75 μm PET films, obtained gel adhesive compositions were put respectively and electrodes were obtained by cutting so that the area portion on which the gel is put is 4 cm² and the area portion on which the gel is not put is 2 cm².

Two electrodes obtained were considered one pair and a pair of electrodes was prepared by attaching gel surfaces together and impedance of electrode pair was measured. The measuring method was conducted conforming to the AAMI (Association for the Advancement of Medical Instrumentation) EC12 Disposable ECG electrodes. The results were shown in Tables 5 and 6.

(Pre-Mixed Solution Stability)

Monomer-mixed solution 4 to 6 stated in Examples and Comparative Examples was obtained and each of the liquid was taken by about 25 ml as a sample into a test tube with a diameter of 20 mm and with a depth of 120 mm, were stored at a room temperature and the generation of separation in 24 hours and 48 hours was observed by visual observation. The results were shown in Tables 5 and 6.

(PET Adhesion)

Each one surface of the PET film of the adhesives obtained by Examples 1 to 20 and Comparative Examples 1, 2 and 6 was peeled off and instead, synthetic paper coated with inorganic filler on one side surface was put followed by cutting into 120 mm in length and 20 mm in width thereby obtaining test strips. PET films remaining on a gel surface of obtained test strips were peeled off and were put on commercially available white PET film (trade name "MERINEX 339" manufactured by Teijin DuPont Films Japan Limited) and were stored for 48 hours at a room temperature, followed by conducting a T type delamination test as in the adhesion test (tensile speed 300 mm/minute). The results were shown in Tables 5 and 6.

(Adhesion on Carbon Surface)

Carbon paste was coated on a surface of commercially available white PET film (trade name "MERINEX 339" manufactured by Teijin DuPont Films Japan Limited) by screen printing and carbon coating films were obtained. Adhesion on carbon surface was measured by the same method as in evaluating PET adhesion except that said carbon coating films were used (gel adhesive compositions were put on a carbon surface) instead of white PET films (trade name "MERINEX 339" manufactured by Teijin DuPont Films Japan Limited) which was used in evaluating PET adhesion. The results were shown in Tables 5 and 6. In addition, as said carbon paste, although composition is optional as long as conductive carbon coating layer can be formed, in the present evaluation, carbon paste which includes polyester binder (trade name "ELECTRODAG 423 SS" manufactured by Acheson Japan Limited) was used.

TABLE 1

| | | | Example | | | | | | |
|---|---|---|---|---|---|---|---|---|---|
| | | | 1 | 2 | 3 | 4 | 5 | 6 | 7 |
| Amphipathic polymer | JMR-10M | A1 | 3 | 12 | 10 | 10 | 5 | 5 | |
| | Rubiscol VA73W | A2 | | | | | | | 15 |
| Water-soluble polymer | JMR-10HH AC60H | | | | | | | | |
| Water | Ion exchange water | B | 8 | 4 | 7 | 7 | 12 | 12 | 7 |
| Water-insoluble polymer | POLYZOL PSA SE-1730 | C1 | | | 5 | 13 | 20 | | 15 |
| | VINYBLAN ADH-1048 | C2 | | | | | | 15 | |
| | VINYBLAN ADH-893T Vinyl acetate emulsion | C3 | | | | | | | |
| Moisturizer | Glycerine | D | 40 | 40 | 37 | 37 | 47 | 38 | 37 |
| Hydrophilic matrix | Hydrophilic monomer Acryl amide | E | 13 | 15 | 20 | 20 | 23 | 20 | 20 |
| | Crosslinkable monomer PDE-400 | G | 0.08 | 0.08 | 0.09 | 0.09 | 0.1 | 0.12 | 0.1 |
| Electrolyte salt | Sodium chloride | F | | 2 | | | 3 | 2 | |
| pH buffer | Citric acid solution (20 wt %) | H | | | | | | | |
| | Citric acid salt solution (20 wt %) | I | | | | | | | |
| Peroxide | Hydrogen peroxide (10 wt %) | J | | | | | | | |
| Surfactant | KH-10 | K | | | | | | | |
| Glycerine content with respect to the total amount excluding water (wt %) | | | 74.5 | 67.2 | 60.1 | 56.4 | 55.9 | 55.4 | 54.7 |

TABLE 2

| | | | Example | | | | | |
|---|---|---|---|---|---|---|---|---|
| | | | 8 | 9 | 10 | 11 | 12 | 13 |
| Amphipathic polymer | JMR-10M | A1 | | 5 | 2 | 10 | 12 | 2.5 |
| | Rubiscol VA73W | A2 | 5 | | | | | |
| Water-soluble polymer | JMR-10HH AC60H | | | | | | | |
| Water | Ion exchange water | B | 13 | 17 | 27 | 7 | 7 | 14 |
| Water-insoluble | POLYZOL PSA SE-1730 | C1 | 18 | | 13 | 13 | 13 | 13 |

TABLE 2-continued

|  |  |  | | Example | | | | | |
|---|---|---|---|---|---|---|---|---|---|
|  |  |  | | 8 | 9 | 10 | 11 | 12 | 13 |
| polymer | VINYBLAN ADH-1048 | | C2 | | | | | | |
|  | VINYBLAN ADH-893T Vinyl acetate emulsion | | C3 | | 14 | | | | |
| Moisturizer | Glycerine | | D | 42 | 39 | 87 | 37 | 37 | 37 |
| Hydrophilic matrix | Hydrophilic monomer | Acryl amide | E | 22 | 20 | 30 | 20 | 20 | 20 |
|  | Crosslinkable monomer | PDE-400 | G | 0.1 | 0.11 | 0.15 | 0.09 | 0.09 | 0.09 |
| Electrolyte salt | Sodium chloride | | F | 2 | | | | | |
| pH buffer | Citric acid solution (20 wt %) | | H | | | | | | |
|  | Citric acid salt solution (20 wt %) | | I | | | | | | |
| Peroxide | Hydrogen peroxide (10 wt %) | | J | | | | 0.4 | | |
| Surfactant | KH-10 | | K | | | | | | |
| Glycerine content with respect to the total amount excluding water (wt %) | | | | 55.2 | 58.1 | 70.1 | 56.4 | 56.1 | 57.7 |

TABLE 3

|  |  |  | | Example | | | | | | |
|---|---|---|---|---|---|---|---|---|---|---|
|  |  |  | | 14 | 15 | 16 | 17 | 18 | 19 | 20 |
| Amphipathic polymer | JMR-10M | | A1 | 10 | 10 | 5 | 5 | 5 | 5 | 5 |
|  | Rubiscol VA73W | | A2 | | | | | | | |
| Water-soluble polymer | JMR-10HH | | | | | | | | | |
|  | AC60H | | | | | | | | | |
| Water | Ion exchange water | | B | 8 | 8 | 12 | 12 | 12 | 12 | 12 |
| Water-insoluble polymer | POLYZOL PSA SE-1730 | | C1 | 20 | 20 | 20 | 20 | 20 | 20 | 20 |
|  | VINYBLAN ADH-1048 | | C2 | | | | | | | |
|  | VINYBLAN ADH-893T Vinyl acetate emulsion | | C3 | | | | | | | |
| Moisturizer | Glycerine | | D | 47 | 47 | 47 | 47 | 47 | 47 | 47 |
| Hydrophilic matrix | Hydrophilic monomer | Acryl amide | E | 23 | 23 | 23 | 23 | 23 | 23 | 23 |
|  | Crosslinkable monomer | PDE-400 | G | 0.1 | 0.1 | 0.1 | 0.1 | 0.1 | 0.1 | 0.1 |
| Electrolyte salt | Sodium chloride | | F | 3 | 3 | 3 | 3 | 3 | 3 | 3 |
| pH buffer | Citric acid solution (20 wt %) | | H | | | 0.1 | 0.25 | 0.5 | 0.5 | 0.5 |
|  | Citric acid salt solution (20 wt %) | | I | | | | | 0.5 | 0.5 | 0.5 |
| Peroxide | Hydrogen peroxide (10 wt %) | | J | 0.4 | 2 | | 0.25 | 0.25 | | |
| Surfactant | KH-10 | | K | | | | | | 0.5 | 1.5 |
| Glycerine content with respect to the total amount excluding water (wt %) | | | | 55.2 | 55.1 | 55.9 | 55.8 | 55.7 | 55.4 | 54.8 |

TABLE 4

|  |  |  | | Comparative Example | | | | | |
|---|---|---|---|---|---|---|---|---|---|
|  |  |  | | 1 | 2 | 3 | 4 | 5 | 6 |
| Amphipathic polymer | JMR-10M | | A1 | | | | | | |
|  | Rubiscol VA73W | | A2 | | | | 10 | | |
| Water-soluble polymer | JMR-10HH | | | | | | | 10 | |
|  | AC60H | | | | | | | 10 | |
| Water | Ion exchange water | | B | 23 | 23 | 15 | 10 | 10 | 21 |
| Water-insoluble polymer | POLYZOL PSA SE-1730 | | C1 | | | | | 20 | |
|  | VINYBLAN ADH-1048 | | C2 | | | | | | |
|  | VINYBLAN ADH-893T Vinyl acetate emulsion | | C3 | | | 20 | 20 | | 3 |

TABLE 4-continued

|  |  |  |  | Comparative Example | | | | | |
|---|---|---|---|---|---|---|---|---|---|
|  |  |  |  | 1 | 2 | 3 | 4 | 5 | 6 |
| Moisturizer | Glycerine |  | D | 35 | 35 | 42 | 42 | 42 | 30 |
| Hydrophilic matrix | Hydrophilic monomer | Acryl amide | E | 20 | 18 | 23 | 23 | 23 | 35 |
|  | Crosslinkable monomer | PDE-400 | G | 0.1 | 0.03 | 0.1 | 0.1 | 0.1 | 0.1 |
| Electrolyte salt | Sodium chloride |  | F | 2.5 | 2.5 | 3 | 8 | 3 | 5 |
| pH buffer | Citric acid solution (20 wt %) |  | H |  |  |  |  |  |  |
|  | Citric acid salt solution (20 wt %) |  | I |  |  |  |  |  |  |
| Peroxide | Hydrogen peroxide (10 wt %) |  | J |  |  |  |  |  |  |
| Surfactant | KH-10 |  | K |  |  |  |  |  |  |
| Glycerine content with respect to the total amount excluding water (wt %) |  |  |  | 60.8 | 60.8 | 53.8 | 52.4 | 52.4 | 41.9 |

TABLE 5

|  |  | Example | | | | | | | | | | | | |
|---|---|---|---|---|---|---|---|---|---|---|---|---|---|
|  |  | 1 | 2 | 3 | 4 | 5 | 6 | 7 | 8 | 9 | 10 | 11 | 12 | 13 |
| Adhesion (g/20 mm) |  | 264 | 248 | 252 | 275 | 320 | 308 | 293 | 311 | 268 | 274 | 282 | 285 | 289 |
| Adhesion to skin |  | 3.0 | 2.9 | 3.0 | 3.8 | 4.7 | 4.0 | 4.0 | 4.3 | 4.0 | 3.2 | 4.0 | 4.0 | 4.0 |
| Compress strength (kPa) |  | 210 | 206 | 243 | 235 | 173 | 210 | 198 | 188 | 189 | 171 | 233 | 228 | 232 |
| Impedance |  | — | 88 | — | — | 118 | 98 | — | 118 | — | — | — | — | — |
| Pre-mixed solution stability | In 24 hours | Good | Good | Good | Good | Good | Good | Good | Good | Good | Good | Good | Good | Good |
|  | In 48 hours | Good | Good | Good | Good | Good | Good | Good | Good | Good | Good | Good | Good | Good |
| PET adhesion | In 48 hours | 280 | 389 | 355 | 362 | 421 | 375 | 475 | 399 | 368 | 221 | 358 | 366 | 328 |
| Adhesion to carbon coat surface | In 48 hours | 1875 | 2002 | 1978 | 1958 | 2196 | 2006 | 2111 | 2112 | 1993 | 1876 | 1919 | 1932 | 2001 |

TABLE 6

|  |  | Example | | | | | | | Comparative Example | | | | | |
|---|---|---|---|---|---|---|---|---|---|---|---|---|---|---|
|  |  | 14 | 15 | 16 | 17 | 18 | 19 | 20 | 1 | 2 | 3 | 4 | 5 | 6 |
| Adhesion (g/20 mm) |  | 312 | 309 | 312 | 316 | 322 | 306 | 317 | 108 | 258 | — | — | — | 95 |
| Adhesion to skin |  | 4.3 | 4.3 | 4.3 | 4.3 | 4.3 | 4.5 | 4.3 | 1.2 | 2.0 | — | — | — | 1.0 |
| Compress strength (8 mm depth) (kPa) |  | 185 | 178 | 181 | 182 | 188 | 177 | 190 | 206 | 58 | — | — | — | 232 |
| Impedance (Ω) |  | 98 | 96 | 102 | 100 | 95 | 97 | 92 | 95 | 76 | — | — | — | 76 |
| Pre-mixed solution stability | In 24 hours | Good | Good | Good | Good | Good | Good | Good | — | — | Separation | Gelation | Gelation | Separation tendency |
|  | In 48 hours | Good | Good | Good | Good | Good | Good | Good | — | — | — | — | — | Separation |
| PET adhesion | In 48 hours | 422 | 419 | 418 | 421 | 419 | 432 | 428 | 78 | 121 | — | — | — | 98 |
| Adhesion to carbon coat surface | In 48 hours | 2251 | 2198 | 2168 | 2172 | 2187 | 2215 | 2196 | 458 | 689 | — | — | — | 552 |

Since Examples 1 and 2 include amphipathic polymer in the matrix of crosslinked water soluble polymer, both PET adhesion and adhesion to a carbon surface were preferable. Likewise, in Examples 3 to 20, obtained gel adhesive compositions had both preferable PET adhesion and adhesion to a carbon surface since they included amphipathic polymer. On the other hand, in Comparative Examples 1, 2, and 6, the values were very low with regard to PET adhesion and adhesion to a carbon surface compared with those in each Example.

Examples 1 to 20 showed preferable value of 248 to 352 (g/20 mm) in measuring adhesion. Further, in sensory evaluation, it was evaluated that the value is higher than the practical level.

Comparative Examples 1 showed results with low sensory values since absolute adhesion is low. Although Comparative Example 2 showed substantially the same measured value as in Example 2, according to the sensory evaluation of adhesion measurement, there were many subjects who felt that adhesion is not enough regarding sensory evaluation on skin adhesion. Further, in Comparative Example 2, when compared with Example 2, compression strength is low of 58 kPa. This shows that the gel is soft, easy to deform, and hard to handle as well as bad in processability. In Comparative Example 6 as well, the result showed that obtained gel adhesive compositions had low sensory evaluation.

From the result of impedance measurement, it is found that by adding salt, provision of conductivity with satisfactory levels required for electrodes for electrocardiogram in which biomedical electrodes, particularly low impedance is needed is available. In addition, according to the AAMI standard, it is required that the average value of electrode pair impedance is not greater than 2 kΩ.

Regarding the stability of pre-mixed solution, any compounding in Examples 1 to 20 is preferably dispersed and satisfactorily available for production up to the point of 24 hours passed. Further, in Examples 17 to 20, although coagulation tendency was generated due to salting out of emulsion by increasing the amount of pH buffering agent to be added, it was found from Examples 19 and 20 that addition of a surfactant realizes dispersal stability. On the other hand, in Comparative Examples, pre-mixed solution of Comparative Example 3 generated separation in 24 hours and in Comparative Examples 4 and 5, gelation like a bavarois generated. In Comparative Example 6, although no separation was observed right after compounding to around 4 hours later, in 24 hours, separation tendency was confirmed by visual observation and further in 48 hours, separation of pre-mixed solution was confirmed by visual observation. In Comparative Examples 3 to 6, stability of pre-mixed solution was all bad.

INDUSTRIAL APPLICABILITY

The gel adhesive compositions of the present invention are preferably used for surgical tapes for putting on an organism, tapes for fixing tubes and the like such as catheters, instillment, and the like, electrodes of electrocardiograms, and other sensing elements, poultices, wound dressing, tapes for fixing artificial anus, and the like, conductive adhesives for electrically contacting electrode element as well as putting electrode element to an organism used for electrocardiogram and other sensors and the like and for electric therapy device conductors, adhesives for fixing magnetic therapy device, support as well as adhesives of transdermal therapeutic system (TTS) and the like. Also, it can be used as adhesives for industrial use such as for building materials, electronic materials, and the like.

Further, the electrodes of the present invention can employ several types of electrode structure due to good adhesion to a surface material which includes polyethylene terephthalate (PET) since gel adhesives comprising amphipathic polymers are included in the gel adhesive layer. Therefore, the electrode of the present invention can preferably be used for an electrode for electro cardiogram examination, an electrode for electrocardiogram for general use, for infants, or for operation rooms, an electrode for TENS, for EMS, or for iontophoresis, a dispersive electrode for scalpels, or an electrode for measuring body fat percentage.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features.

What is claimed is:

1. A gel adhesive composition containing a crosslinked water-soluble polymer, water, a moisturizer, a water-insoluble polymer having adhesiveness and an amphipathic polymer, wherein the water-insoluble polymer having adhesiveness is contained in an amount of not less than 3% by weight with respect to the total amount of the composition except water, and wherein the amphipathic polymer is contained in an amount of 0.05 to 7.0% by weight with respect to the total amount of the composition except water, and wherein the water-insoluble polymer is dispersed throughout the gel adhesive composition and wherein the water-insoluble polymer having adhesiveness is a copolymer of a hydrophobic monomer and a hydrophilic monomer having copolymerization ratio of the hydrophilic monomer of 0.1 to 5% by weight.

2. The gel adhesive composition according to claim 1, wherein the moisturizer is contained in an amount of 50 to 80% by weight with respect to the total amount of the composition except water.

3. The gel adhesive composition according to claim 1 further containing an electrolytic salt in an amount of 0.5% by weight or higher with respect to the total amount of the composition except water.

4. The gel adhesive composition according to claim 1, wherein the crosslinked water-soluble polymer composes the matrix of the composition.

5. The gel adhesive composition according to claim 1, wherein the water-insoluble polymer is an emulsion of a water-insoluble polymer.

6. The gel adhesive composition according to claim 1, wherein the crosslinked water-soluble polymer is a copolymer of a water-soluble (meth)acrylic monomer and a crosslinkable monomer having two or more alkenyl groups and is contained in an amount of 15 to 35% by weight with respect to the total amount of the gel adhesive composition except water, and the moisturizer is polyvalent alcohol and contained in an amount of 50 to 80% by weight with respect to the total amount of the gel adhesive composition except water.

7. A gel adhesive composition containing a crosslinked water-soluble polymer, water, a moisturizer, an amphipathic polymer, a water-insoluble polymer having adhesiveness, and an electrolytic salt, wherein the composition contains water in an amount of 13 to 40% by weight with respect to the total amount of the composition, and the crosslinked water-soluble polymer 15 to 35% by weight, the water-insoluble polymer 3 to 20% by weight, the amphipathic polymer 0.05 to 7.0% by weight, the moisturizer 50 to 80% by weight, and the electrolytic salt 0.5 to 6.0% by weight with respect to the total amount of the composition except water, and the crosslinked water-soluble polymer is a copolymer of a water-soluble (meth)acrylic monomer and a crosslinkable monomer having two or more alkenyl groups, the moisturizer is polyvalent alcohol, and the water-insoluble polymer is polymerization of one or more hydrophobic monomers such as hydrophobic monomer alone or polymerizations thereof, and wherein the water-insoluble polymer having adhesiveness is a copolymer of a hydrophobic monomer and a hydrophilic monomer having copolymerization ratio of the hydrophilic monomer of 0.1 to 5% by weight.

8. A manufacturing method of a gel adhesive composition comprising the following steps:
  (a) mixing a pre-mixed solution containing a non crosslinkable monomer, a crosslinkable monomer, a moisturizer, water, a water-insoluble polymer having adhesiveness, and an amphipathic polymer and
  (b) carrying out polymerization by heating or radiating light to the mixed pre-mixed solution,
  wherein the water-insoluble polymer having adhesiveness is contained in an amount of not less than 3% by weight with respect to the total amount of the composition except water,
  wherein the amphipathic polymer is contained in an amount of 0.05 to 7.0% by weight with respect to the total amount of the pre-mixed solution except water,
  wherein the water-insoluble polymer is dispersed throughout the pre-mixed solution, and
  wherein the water-insoluble polymer having adhesiveness is a copolymer of a hydrophobic monomer and a hydrophilic monomer having copolymerization ratio of the hydrophilic monomer of 0.1 to 5% by weight.

9. The manufacturing method of a gel adhesive composition according to claim 8 comprising a step of adjusting pH of the pre-mixed solution at 4 to 7 in the step (a).

10. The manufacturing method of a gel adhesive composition according to claim 8, wherein the hydrophilic monomer is an acrylic acid alkyl ester.

11. The manufacturing method of a gel adhesive composition according to claim 8, wherein the amphipathic polymer is poly(vinyl alcohol) saponified at 50 to 75%.

12. The manufacturing method of a gel adhesive composition according to claim 8, wherein a surfactant is further added properly to the pre-mixed solution so as to adjust the amount in a range of 0.1 to 2.0% by weight with respect to the total amount of the pre-mixed solution.

13. The manufacturing method of a gel adhesive composition according to claim 8, wherein a peroxide 0.003 to 0.3% by weight is further added to the mixed pre-mixed solution and mixed and dissolved and then polymerization is carried out.

14. The manufacturing method of a gel adhesive composition according to claim 8, wherein the water-insoluble polymer is an emulsion using water as a dispersant.

15. A pre-mixed solution for a gel adhesive composition containing a non crosslinkable monomer, a crosslinkable monomer, a moisturizer, water, a water-insoluble polymer having adhesiveness, and an amphipathic polymer,
  wherein the water-insoluble polymer having adhesiveness is contained in an amount of not less than 3% by weight with respect to the total amount of the composition except water,
  wherein the amphipathic polymer is contained in an amount of 0.05 to 7.0% by weight with respect to the total amount of the pre-mixed solution except water,
  wherein the water-insoluble polymer is dispersed throughout the pre-mixed solution, and
  wherein the water-insoluble polymer having adhesiveness is a copolymer of a hydrophobic monomer and a hydrophilic monomer having copolymerization ratio of the hydrophilic monomer of 0.1 to 5% by weight.

16. The pre-mixed solution for a gel adhesive composition according to claim 15, wherein the water-insoluble polymer is contained in an amount of 3 to 20% by weight of the total amount of the composition except water.

17. An electrode comprising a gel adhesive layer, wherein the gel adhesive layer contains a gel adhesive composition, wherein the gel adhesive composition contains a crosslinked water-soluble polymer, water, a moisturizer, a water-insoluble polymer having adhesiveness, and an amphipathic polymer,
  wherein the water-insoluble polymer having adhesiveness is contained in an amount of not less than 3% by weight with respect to the total amount of the composition except water,
  wherein the amphipathic polymer is contained in an amount of 0.05 to 7.0% by weight with respect to the total amount of the composition except water,
  wherein the water-insoluble polymer is dispersed throughout the eel adhesive composition, and
  wherein the water-insoluble polymer having adhesiveness is a copolymer of a hydrophobic monomer and a hydrophilic monomer having copolymerization ratio of the hydrophilic monomer of 0.1 to 5% by weight.

18. An electrode comprising
  a polyethylene terephthalate layer composing a sheet-like surface substrate;
  a pair of carbon coat layers arranged in the rear face of the polyethylene terephthalate layer at an interval and connected to a pair of electrode terminals, respectively, and composing an electrode element part; and
  gel adhesive layers respectively stretched over the rear faces of the pair of the carbon coat layers and the rear face of the polyethylene terephthalate layer positioned between the pair of the carbon coat layers, wherein the gel adhesive layers contain the gel adhesive composition, wherein the gel adhesive composition contains a crosslinked water-soluble polymer, water, a moisturizer, a water-insoluble polymer having adhesiveness, and an amphipathic polymer contained in an amount of 0.05 to 7.0% by weight with respect to the total amount of the composition except water,
  wherein the water-insoluble polymer having adhesiveness is contained in an amount of not less than 3% by weight with respect to the total amount of the composition except water,
  wherein the water-insoluble polymer is dispersed throughout the gel adhesive composition, and
  wherein the water-insoluble polymer having adhesiveness is a copolymer of a hydrophobic monomer and a hydrophilic monomer having copolymerization ratio of the hydrophilic monomer of 0.1 to 5% by weight.

* * * * *